US012128129B2

(12) United States Patent
Pesaro et al.

(10) Patent No.: US 12,128,129 B2
(45) Date of Patent: Oct. 29, 2024

(54) ***LACTOBACILLUS PLANTARUM* FOR SKIN CARE**

(71) Applicants: SYMRISE AG, Holzminden (DE); PROBI AB, Lund (SE)

(72) Inventors: Manuel Pesaro, Holzminden (DE); Dominik Stuhlmann, Holzminden (DE); Lisa Garbe, Holzminden (DE); Gerhard Schmaus, Höxter-Bosseborn (DE); Kerstin Holmgren, Helsingborg (SE); Niklas Larsson, Lund (SE)

(73) Assignees: SYMRISE AG, Holzminden (DE); PROBI AB, Lund (SE)

( * ) Notice: Subject to any disclaimer, the term of this patent is extended or adjusted under 35 U.S.C. 154(b) by 562 days.

(21) Appl. No.: 17/254,347

(22) PCT Filed: Jun. 26, 2019

(86) PCT No.: PCT/EP2019/067007
§ 371 (c)(1),
(2) Date: Dec. 21, 2020

(87) PCT Pub. No.: WO2020/002429
PCT Pub. Date: Jan. 2, 2020

(65) Prior Publication Data
US 2022/0233430 A1    Jul. 28, 2022

(30) Foreign Application Priority Data
Jun. 26, 2019    (WO) .................. PCT/EP2018/067090

(51) Int. Cl.
*A61K 8/99*        (2017.01)
*A61G 19/00*       (2006.01)
(Continued)

(52) U.S. Cl.
CPC ................ *A61K 8/99* (2013.01); *A61G 19/00* (2013.01); *A61K 8/0225* (2013.01); *A61K 9/14* (2013.01);
(Continued)

(58) Field of Classification Search
CPC .......... A61K 8/99; A61K 8/0225; A61K 9/14; A61K 35/747; A61Q 19/00; A61P 17/00; A61P 29/00
See application file for complete search history.

(56) References Cited

U.S. PATENT DOCUMENTS 7,510,734 B2    3/2009 Sullivan et al.
7,807,440 B2    10/2010 Molin et al.
(Continued)

FOREIGN PATENT DOCUMENTS

CN    1357038 A    7/2002
CN    101190239 A  6/2008
(Continued)

OTHER PUBLICATIONS

NIH, "Atopic Dermatitis", 2022 from https://www.niams.nih.gov/health-topics/atopic-dermatitis/diagnosis-treatment-and-steps-to-take (Year: 2022).*
(Continued)

*Primary Examiner* — Bethany P Barham
*Assistant Examiner* — Ayaan A Alam
(74) *Attorney, Agent, or Firm* — POLSINELLI PC

(57) ABSTRACT

The present invention relates to microorganisms for use in the treatment and/or prevention of skin conditions by topical application. In particular, the microorganisms are for use in the treatment and/or prevention of loss of skin barrier function, inflammatory conditions and/or growth of pathogenic microorganism. The invention further relates to pharmaceutical or cosmetic compositions or products compris-
(Continued)

ing the microorganisms Provided is also a cosmetic use of the microorganisms or compositions for application on the skin and a cosmetic method, in particular to improve the appearance of the skin.

17 Claims, 13 Drawing Sheets

(51) Int. Cl.
  A61K 8/02      (2006.01)
  A61K 9/14      (2006.01)
  A61K 35/747    (2015.01)
  A61P 17/00     (2006.01)
  A61P 29/00     (2006.01)
  A61Q 19/00     (2006.01)
(52) U.S. Cl.
  CPC ............ A61K 35/747 (2013.01); A61P 17/00 (2018.01); A61P 29/00 (2018.01)

(56) References Cited

U.S. PATENT DOCUMENTS

| | | |
|---|---|---|
| 9,028,841 B2 | 5/2015 | Henn et al. |
| 9,687,513 B2 | 6/2017 | Alenfall et al. |
| 2005/0196480 A1 | 9/2005 | Sullivan et al. |
| 2008/0268006 A1 | 10/2008 | Molin et al. |
| 2009/0208469 A1 | 8/2009 | Alenfall et al. |
| 2009/0324563 A1 | 12/2009 | Muroyama et al. |
| 2010/0028449 A1 | 2/2010 | Prakash et al. |
| 2011/0262372 A1 | 10/2011 | Hsieh et al. |
| 2013/0209374 A1 | 8/2013 | Castellana |
| 2014/0023620 A1 | 1/2014 | Ioudina |
| 2014/0065218 A1 | 3/2014 | Lang et al. |
| 2014/0199281 A1 | 7/2014 | Henn et al. |
| 2015/0238548 A1 | 8/2015 | Huang et al. |
| 2015/0240200 A1 | 8/2015 | Tsai et al. |
| 2015/0250834 A1 | 9/2015 | Tsai et al. |
| 2015/0328141 A1 | 11/2015 | Reindl et al. |
| 2017/0224750 A1 | 8/2017 | Callanan et al. |
| 2017/0306289 A1 | 10/2017 | Chung et al. |
| 2019/0037902 A1 | 2/2019 | Fischer et al. |
| 2019/0247295 A1* | 8/2019 | Chen ..................... A61Q 19/08 |

FOREIGN PATENT DOCUMENTS

| | | | |
|---|---|---|---|
| CN | 101252943 A | 8/2008 | |
| CN | 101703179 A | 5/2010 | |
| CN | 101715908 A | 6/2010 | |
| CN | 102245191 A | 11/2011 | |
| CN | 102438637 A | 5/2012 | |
| CN | 102470151 A | 5/2012 | |
| CN | 104814983 A | 8/2015 | |
| CN | 104958187 A | 10/2015 | |
| DE | 202009011379 U1 | 12/2010 | |
| EP | 0904784 A1 | 3/1999 | |
| EP | 1634948 A1 | 3/2006 | |
| EP | 1955702 A1 | 8/2008 | |
| EP | 2364712 A1 | 9/2011 | |
| EP | 2420580 A1 | 2/2012 | |
| JP | H0517363 A | 1/1993 | |
| JP | 2007526325 A | 9/2007 | |
| JP | 2008502714 A | 1/2008 | |
| JP | 2008518588 A | 6/2008 | |
| JP | 2012025699 A | 2/2012 | |
| JP | 2014516957 A | 11/2012 | |
| JP | 2014000039 A | 1/2014 | |
| JP | 2019506181 A | 3/2019 | |
| JP | 6538286 B2 | 7/2019 | |
| KR | 1020120035923 A | 4/2012 | |
| RU | 2492851 C1 | 9/2013 | |
| WO | 0078322 A2 | 12/2000 | |
| WO | WO-2007040446 A1 * | 4/2007 | ............. A21D 13/02 |
| WO | 2008018143 A1 | 2/2008 | |
| WO | 2010077795 A2 | 7/2010 | |
| WO | 2010099824 A1 | 9/2010 | |
| WO | 2012022773 A1 | 2/2012 | |
| WO | 2012033151 A1 | 3/2012 | |
| WO | 2010064373 A1 | 5/2012 | |
| WO | 2012156491 A1 | 11/2012 | |
| WO | 2014140080 A1 | 9/2014 | |
| WO | 2016023688 A1 | 2/2016 | |
| WO | 2017035412 A1 | 3/2017 | |
| WO | 2017125447 A1 | 7/2017 | |
| WO | 2017125453 A1 | 7/2017 | |

OTHER PUBLICATIONS

European Office Action issued on Mar. 12, 2021 for corresponding European Application No. 18702144.9.
Mette Kirstine Keller et al., "Co-aggregation and growth inhibition of probiotic lactobacilli and clinical isolates of mutans streptococci: An in vitro study," Acta Odontologica Scandinavica, vol. 69, 2011, pp. 263-268 XP009162555.
Zhihong Sun et al., "Expanding the biotechnology potential of lactobacilli through comparative genomics of 213 strains and associated genera," Nature Communications, 2015, pp. 1-13 XP002769022.
S. Resta-Lenert et al., "Live probiotics protect intestinal epithelial cells from the effects of infection with enteroinvasive Escherichia coli (EIEC)," Inflammatory Bowel Disease, vol. 52, 2003, pp. 988-997 XP055678154.
Tamara Smokvina et al., "*Lactobacillus paracasei* Comparative Genomics: Towards Species Pan-Genome Definition and Exploitation of Diversity," PLoS One, vol. 8, Issue 7, 2013, pp. 1-18 XP055711380.
C. Lang et al., "Specific Lactobacillus/Mutans Streptococcus Co-aggregation," Research Reports, vol. 89, No. 2, 2009, pp. 175-180 XP009162445.
New Zealand Office Action issued on Nov. 11, 2021 for corresponding New Zealand Application No. 744342.
Japanese Office Action issued on Dec. 21, 2022 for corresponding Japanese Application No. 2021-196237.
International Search Report and Written Opinion issued on Oct. 17, 2019 for corresponding PCT Application No. PCT/EP2019/067007.
Japanese Office Action issued on Jan. 14, 2021 for corresponding Japanese Application No. 2018-538221.
Non-Final Office Action issued on Mar. 18, 2021 in co-pending U.S. Appl. No. 16/478,514.
Non-Final Office Action issued on Sep. 18, 2020 in the co-pending U.S. Appl. No. 16/070,553.
Johannes Snel et al., "Competitive Selection of Lactic Acid Bacteria That Persists in the Human Oral Cavity", Applied and Environmental Microbiology, vol. 77, No. 23, 2011, pp. 8445-8450.
Office Action issued on Apr. 2, 2020 in co-pending U.S. Appl. No. 16/070,553.
International Search Report and Written Opinion issued on Mar. 17, 2017 in corresponding PCT Application No. PCT/ EP2017/051005.
Biogrowing: "Dietary Supplements", 2010, pp. 1-3, XP002758028.
Li, Allen, "Biogrowing probiotics brochure", 2015, p. 1, XP002758029.
Iqbal, S. et al., "β-Galactosidase from Lactobacillus plantarum WCFS1: biochemical characterization and formation of prebiotic galacto-oligosaccharides," Carbohydrate Research, vol. 345, 2010, pp. 1408-1416.
International Preliminary Report on Patentability issued Jul. 24, 2018 for corresponding PCT Application No. PCT/EP2017/051011.
International Search Report and Written Opinion issued on Mar. 10, 2017 for corresponding PCT Application No. PCT/EP2017/051011.
Anonymous: "Biogrowing—comprehensive probiotic solutions provider," 2015, XP002759385, pp. 1-16 www.biogrowing.com.
Sookkhee, S. et al., "Lactic acid bacteria from healthy oral cavity of Thai volunteers: Inhibition of oral pathogens," Journal of Applied Microbiology, vol. 90, No. 2, 2001, pp. 172-179.
Vuotto, Claudia et al., "Probiotics to counteract biofilm-associated infections: promising and conflicting data," International Journal of Oral Science, vol. 6, No. 4, 2014, pp. 189-194.

(56) References Cited

OTHER PUBLICATIONS

Chuang, Li-Chuan et al., "Probiotic effect on cariogenic bacterial flora," Clinical Oral Investigations, vol. 15, No. 4, 2010, pp. 471-476.
Korean Office Action issued on Oct. 18, 2018 for corresponding Korean Patent Application No. 10-2018-7023803.
Chinese Office Action issued on Jan. 11, 2019 for corresponding Chinese Patent Application No. 201780007278.3.
Chinese Office Action issued on Apr. 3, 2019 for corresponding Chinese Application No. 201780007278.3.
Kistler, James O. et al.; "Development and pyrosequencing analysis of an in-vitro oral biofilm model," BMC Microbiology; 2015, pp. 1-10.
Japanese Office Action issued on Dec. 10, 2018 for corresponding JP Application No. JP 2018-538205.
Australian Office Action issued on Sep. 10, 2018 for corresponding AU Application No. 2017208481.
European Office Action issued on Mar. 8, 2018 for corresponding EP Application No. EP 16151963.2.
Written Opinion issued on Mar. 22, 2019 for corresponding PCT Application No. PCT/EP2018/067090.
Written Opinion issued on Jul. 27, 2017 for corresponding PCT Application No. PCT/EP2017/051003.
International Search Report and Written Opinion issued on Mar. 16, 2018, for corresponding PCT Application No. PCT/EP2018/051112.
Snel, J. et al., "Competitive Selection of Lactic Acid Bacteria That Persists in the Human Oral Cavity", Applied and Environmental Microbiology, vol. 77, No. 23, 2011, pp. 8445-8450 XP055379435.
Roy, Byun et al., "Quantitative analysis of diverse *Lactobacillus* species present in advanced dental caries", Journal of Clinical Microbiology, American Society of Microbiology, vol. 42, No. 7, 2004, pp. 3128-3136 XP002488329.
Azcarate-Peril, M. A. et al., "Analysis of the Genome Sequence of Lactobacillus gasseri ATCC 33323 Reveals the Molecular Basis of an Autochthonous Intestinal Organism", Applied and Environmental Microbiology, vol. 74, No. 15, 2008, pp. 4610-4625 XP055029769.
Russian Search Report issued on Mar. 26, 2020 for corresponding Russian Application No. 2018129759/04.
Roalnd J. Siezen et al., "Genomic diversity and versatility of Lactobacillus plantarum, a natural metabolic engineer," Microbial Cell Factories, vol. 10, 2011, pp. 1-13.
Stefan R. Herbel et al., "Timely approaches to identify probiotic species of the genus Lactobacillus," Gut Pathogens, vol. 5, No. 27, 2013, pp. 1-13.
Declaration by Dr. Niklas Larsson, 2020, pp. 1-15.
Juliana M. Ansari et al., "Strain-level diversity of commercial probiotic isolates of *Bacillus, Lactobacillus*, and *Saccharomyces* species illustrated by molecular identification and phenotypic profiling," Research article, 2019, pp. 1-19.
Office Action issued on Oct. 18, 2019 in co-pending U.S. Appl. No. 16/070,573.
Chinese Office Action issued on Oct. 26, 2022 for corresponding Chinese Application No. 201880007393.5.
Chinese Office Action issued on Dec. 6, 2021 for corresponding Chinese Application No. 20178007163.4.
Japanese Office Action issued on Mar. 13, 2023 for corresponding Japanese Application No. 2020-573258.
Chinese Office Action issued on Dec. 29, 2023 for corresponding Chinese Application No. 201980040544.1.
U.S. Appl. No. 16/070,553, filed Jul. 17, 2018.
U.S. Appl. No. 16/478,514, filed Jul. 17, 2019.
U.S. Appl. No. 16/070,573, filed Jul. 17, 2018.

\* cited by examiner

LACTOBACILLUS PLANTARUM FOR SKIN CARE

CROSS-REFERENCE TO RELATED APPLICATIONS

This application is a national stage application (under 35 U.S.C. § 371) of PCT/EP2019/067007, filed Jun. 26, 2019, which claims benefit of PCT Application No. PCT/EP2018/067090, filed Jun. 26, 2018, which are incorporated herein by reference in their entireties.

The present invention relates to microorganisms for use in the treatment and/or prevention of skin conditions by topical application, wherein the microorganisms are selected from the group consisting of *Lactobacillus plantarum* HEAL 19 (DSM 15313) and *Lactobacillus plantarum* HEAL 99 (DSM 15316). In particular, the microorganisms are for use in the treatment and/or prevention of loss of skin barrier function, inflammatory skin conditions and/or growth of pathogenic microorganism. The invention further relates to a particulate preparation comprising the microorganism(s) and a carrier as well as pharmaceutical or cosmetic compositions or products comprising the microorganisms. Provided is also a cosmetic use of the microorganisms or compositions for application on the skin and a cosmetic method, in particular to improve the appearance of the skin and/or prevent body odor.

Probiotics are well known to improve gut well-being, attributed to the rise of the gut-brain axis correlations, alleviate lactose intolerance, are beneficial in vaginal or urogenital infection treatment or prevent inflammatory bowel disease. Especially *Lactobacillus* sp. has a safe and long tradition in food fermentation processes. In contrast to the gut, little is known about the interactions between epidermis, skin microbiota and environmental microorganisms.

Nowadays more and more studies show that probiotics exert other health promoting effects including skin health. Bifidobacteria and Lactic acid bacteria are the most common types of probiotics used and the area of skin care using these has been actively developed over the last years.

However, not all probiotic strains show beneficial effects on skin and single strains are rarely mentioned. And even if, the balance between an anti-inflammatory or other effects as an active component in a cosmetic composition and the non-causing of any pro-inflammation side effects by the microorganism itself needs to be given.

The skin is continuously exposed to bacteria, microorganisms and potential pathogens. To avoid infections or invasion of these pathogenic bacteria the skin has developed multifaceted defense strategies. Beside the physical and chemical barrier of the stratum corneum it includes the constitutive and inductive AMP barrier, which is essential in this context (Harder et al. 2013, Wiesner and Vilcinskas 2010).

Antimicrobial peptides (AMP) are a diverse and abundant group of molecules. Characteristic are the small size, amino acid composition, amphipathicity and/or cationic charge. On the basis of their amino acid composition they are often divided into characteristic sub-groups. Their diversity of antimicrobial potential and mechanism of action is as diverse as their structure and composition. They can be detected in various tissues and cell types of invertebrates, animal species and plants (Brogden 2005, Zasloff 2002). In human skin they serve as first defense line, as they are active against a broad spectrum of Gram positive and Gram negative bacteria, fungi, eukaryotic parasites and/or viruses (Brown and Hancock 2006).

The AMP expression can be up-regulated in response to various environmental stimuli like contact to pathogens or intracellular inflammation pathways. Commensal and pathogenic bacteria differ in their ability to induce AMP expression and activate different signaling pathways in human skin to innate human immunity. Little is known about the specific interactions between both. Beta-Defensins for example are upregulated by various stimuli of inflammation and/or infections, like interleukin 1 or bacterial lipopolysaccharide (Chung and Dale 2004). Mahe et al. (US2009/0035294 A1) disclose that LPS from *Vitreoscilla filiformis* comprising Lipid A has the ability to stimulate the expression of AMPs in keratinocytes without having pathogenic activity.

It is known that the skin microbiome can play a key role in various skin diseases and/or health conditions. The complexity and inter/intra-individual variety of the microbiome as well as the difficulties in characterizing, categorizing, and analyzing are the challenges in understanding interactions and developing topical therapeutic and/or diagnostic applications and/or treatments that helps to influence, interact and/or support the microbiome. Nevertheless, the microbiome and microbiome-related diseases have become a more and more important aspect and induce a need for developing microbiome-related treatments of diseases and health conditions.

Atopic dermatitis (AD) for instance is a multifunctional complex disorder with various genetic risk factors but significant environmental triggers. AD is associated with a physical barrier defects and/or dysbioses (microbial imbalance). Patients exhibit suppression of various AMPs like Cathelicidin or β-Defensin or alternations in T-cell homeostasis. The combination of antimicrobial and physical barrier defects likely pushes the dysbiosis leading to further disruption of the cellular immunity balance, which is again necessary to establish the balance with the external environment (Ong et al. 2002, Palmer et al 2006, Sakaguchi et al. 2010).

Moreover, other common human skin diseases such as rosacea or psoriasis are associated with dysregulated AMP-expression as well. By specific manipulation and induction of these endogenous peptides a balanced skin microbiome can be restored, maintained and/or improved. This represents a new strategy to create skin benefits in a broad range of application fields.

In addition, it is known that *Staphylococcus aureus* is frequently found in eczemous skin lesions of AD patients and seems to be important and responsible for aggravating the disease status. Skin that is inflamed or damaged by scratching, sunburn or other trauma is more likely to become infected. Dry skin for instance becomes easily damaged as well. The avoidance of this kind of infection shows a second highly relevant starting point in developing alternative therapeutic treatments.

From the state of the art some publications are known as dealing with various beneficial effects of probiotics for skin care and skin health. *Lactobacillus* preparations have been used in cosmetic applications for diverse purposes. These are mainly based on health benefits for skin, body, hair or nails but also relate to technical application. Most described compositions contain a mixture of different living or non-viable probiotic strains, preferably used in combination with fermented plants, foods or chemical agents. On the other hand, the beneficial effects of single pure culture strains have rarely been shown.

In WO2013153358, the use of *Lactobacillus reuteri*, *Lactobacillus rhamnosus* and *Bifidobacterium longum* for cosmetic application and topical skin treatment is described.

WO2015048511 discloses watery lotion compositions for topical application that contain an extract from fermentation of probiotic microorganisms, including the genera *Lactobacillus* or *Bifidobacterium*.

Beneficial effects of microorganisms for skin barrier function have been described in WO2009031106. Disclosed is the cosmetic use of at least one probiotic microorganism/fractions in combination with hesperidin for preventing a reduction in and/or reinforcing the barrier function of the skin.

The possibility of β-Defensin induction in skin cells by two *L. plantarum* strains is described in WO2005091933. Antimicrobial effects are shown on skin as well as improvement in acne and sensitive skin.

US2014186409 describes the cosmetic use of lactic acid bacteria and/or compositions containing them for topical treatment and/or prevention of skin infections, chronic wound or skin diseases caused by pathogenic microorganism like *S. aureus* or *Pseudomonas aeruginosa*. The efficacy is caused by specific bacterial co-aggregation of lactic acid bacteria with pathogens.

In WO2010056198, a pharmaceutical preparation is disclosed comprising a combination of diverse viable alpha-*Streptococcus* and *Lactobacillus* strains that is useful for the treatment of *Staphylococcus* induced infections on human skin.

WO2005077391 discloses a formulation comprising at least two lactic acid bacteria strains, selected from a pool that includes *L. plantarum* for treatment and/or prevention of stress-induced inflammatory disorder. Claimed effects for topical application are restricted to severely injured skin, i.e. wounds due to ulcers or burns.

Topical application of *Lactobacillus plantarum* on severe human burns has been described to improve tissue repair and prevent infections (Peral et al. 2009).

KR2011134151 discloses a large range of lactic acid bacteria, including *Lactobacillus plantarum*, which produce active substances, especially bacteriocin or bacteriocin-like substances. The strains are suggested to be used in prevention and treatment of bacterial caused skin infections or inflammatory skin diseases, such as atopic dermatitis or acne.

WO2016023688 describes compositions for use in the prevention or treatment of skin infections comprising *Lactobacillus plantarum* CNCM 1-4026. In particular, it was found that the concentrated supernatant collected after the *Lactobacillus* fermentation inhibited or delayed the growth of different Gram positive and Gram negative bacteria, inter alia *Staphylococcus aureus* or *Staphylococcus epidermidis*. Only soluble bacterial components obtained from the growth medium were used, but not the entire bacterial cells.

Inhibition effects of *Staphylococcus aureus* with different lactic acid bacteria, including *Lactobacillus plantarum*, have been observed using cell free supernatants as well as extracts (Yong et al 2015).

WO2017125447A1 relates to microorganisms for use in the treatment and prevention of inflammation in the oral cavity, in particular to treat or prevent gingivitis and periodontitis. Among the microorganisms disclosed, *Lactobacillus plantarum* HEAL 19 is shown to have an anti-inflammatory effect on monocytes. However, it cannot be concluded from WO2017125447A1 that such effects extend to epidermal skin cells outside the oral cavity, i.e. non-mucosal keratinocytes. Since non-mucosal skin has a completely different structure, in particular with regard to protective layers (e.g. stratum corneum) and the associated strong barrier function, it cannot be expected that the same effects that were observed on monocytes would apply on skin. Furthermore, epidermis is a non-vascularized tissue that does not contain any monocytes or related cell forms at all.

It was an objective of the present invention to provide probiotic bacterial strains that are useful in the treatment and/or prevention of skin conditions, in particular loss of skin barrier function, inflammatory skin conditions and growth of pathogenic microorganisms.

It was a further objective of the present invention to provide probiotic bacterial strains that are useful in for cosmetic applications, in particular capable to improve the appearance of the skin and prevent body odor.

In particular, it was also an objective, that the strains provided by the present invention have one or preferably two, several or all of the effects selected from strengthening the skin barrier, soothing the skin and reducing or preventing inflammation, increasing the skin's immune defense by up-regulating AMPs, slowing skin ageing, inhibit the growth of pathogenic microorganisms on the skin and preventing infections.

Furthermore, the provided strains should have no undesirable side-effects, such as pro-inflammatory effects, when used on the skin.

The above objectives are met by a microorganism or mixture comprising or consisting of two microorganisms for use in the treatment and/or prevention of skin conditions by topical application, wherein the microorganism(s) is/are selected from the group consisting of *Lactobacillus plantarum* HEAL 19 (DSM 15313) and *Lactobacillus plantarum* HEAL 99 (DSM 15316).

According to the present invention, in any embodiment, either one or a mixture of both of the *Lactobacillus plantarum* strains HEAL 19 and HEAL 99 and can be used. The expression "microorganism or mixture comprising or consisting of two microorganisms" therefore refers to either one of the two strains being present or both strains being present.

It was known from the prior art, that some probiotic bacteria are capable to improve certain aspects of skin conditions and skin appearance, but not all bacterial strains provide beneficial effects on the skin and some may even be detrimental. Moreover, beneficial effects have been shown for the application of microorganisms on severely injured or burned skin as well as the mucosa in the oral cavity. However, these effects cannot be transferred to or compared with applications on non-mucosal skin, which has a strong barrier function. To induce effects described in the present invention the existence of a skin barrier is a prerequisite.

It has now been found out that *Lactobacillus plantarum* HEAL 19 and HEAL 99 offer a unique combination and comprehensive field of activity, which helps to decisively improve clinical symptoms and cosmetic appearance of the skin, but also support healthy skin and prevent abnormalities. It is shown that the topical application of these strains provide a combination of supporting the skin's barrier by induction of various AMPs but also strengthening the physical skin barrier by a number of pathways, beside its anti-inflammatory capacity. In addition, growth inhibition effects of *Staphylococcus aureus* could also be demonstrated for the described *Lactobacillus plantarum* strains.

It has been shown that, in particular, the heat-treated *Lactobacillus* spp., including both water soluble and water insoluble components are able to improve skin health. Bacteria suspensions have the potential to strengthen skin's physical barrier by reducing transepidermal water loss (TEWL) and/or increasing components related to the natural moisturizing factor. At the same time, the skin's productions of various AMPs is induced, boosting the skin's self-defense. Potential infections of the skin can be prevented by inhibiting growth of pathogens, like *S. aureus*. Additionally, *L. plantarum* HEAL 19 and HEAL 99 revealed anti-inflammatory effects.

In conclusion, *L. plantarum* HEAL 19 and 99 strains show high and comprehensive potential as agents to modify dermal properties and skin health when applied topically.

In the context of the present invention the term "skin" refers to skin that is non-mucosal skin. In particular, the mucosa found in cavities of the body such as e.g. the oral cavity, the gastric, intestinal, bronchial, anal or vaginal mucosa is not covered by the term "skin". Accordingly, the term "topical application" refers to the application of an agent and/or formulation on the skin and excludes any applications in the inside of body cavities, which are covered with mucosa. Preferably, the skin still retains a protective function which has not been significantly compromised, e.g. by severe injury or burns.

"By topical application" in the context of the present invention means that the microorganism(s), or the preparation(s), the pharmaceutical or cosmetic compositions(s) or product(s) comprising the microorganism(s) as described herein, are administered directly by topical application on the skin, i.e. directly to the surface of the skin.

"Skin condition" in the context of the present invention refers to any state of the skin that is associated with medical conditions of the skin, preferably other than injury or burns. "Skin condition" preferably relates to a status characterized by discomfort such as itching or represents a cosmetic problem such as flaking, dryness, redness, rashes, acne, oilyness or body odor due to bacterial growth. Examples of skin conditions are given below.

The strain *Lactobacillus plantarum* HEAL 19 as been deposited under the Budapest Treaty at the Leibniz Institut Deutsche Sammlung für Mikroorganismen und Zellkulturen GmbH (DSMZ), Inhoffenstr. 7B, 38124 Braunschweig, Germany, under the accession number DSM 15313 by Probi AB, Sölvegatan 41, 223 70 Lund, Sweden on 27 Nov. 2002. The strain *Lactobacillus plantarum* HEAL 99 has been deposited under the Budapest Treaty at the Leibniz Institut Deutsche Sammlung fur Mikroorganismen und Zellkulturen GmbH (DSMZ), Inhoffenstr. 7B, 38124 Braunschweig, Germany, under the accession number DSM 15316 by Probi AB, Sölvegatan 41, 223 70 Lund, Sweden on 27 Nov. 2002.

In a preferred embodiment, the microorganism(s) has/have been subjected to a heat-treatment, which preferably led to inactivation, attenuation or death of the microorganisms. Preferably, the heat-treated microorganism(s) have an intact physical structure.

The heat-treatment may be performed by ultrasound, UV-irradiation or heating. Preferably it is performed by heating to a temperature from 60 to 121° C. for 1 second to 120 minutes, such as from 20 seconds to 120 minutes. In a preferred embodiment, heat-treatment is performed between 70 and 100° C. for 20 seconds to 15 minutes, preferably using an industrial pasteurizer. Preferably, the microorganism(s) is/are dead and can thus no longer be propagated. Preferably, the heat-treated microorganisms still have an intact physical structure, meaning that cellular structures are not destroyed by the heat-treatment and the microorganisms can be delivered containing metabolites. Advantageously, during the heat-treatment, the microorganisms typically maintain their ability to confer beneficial effects for treating skin conditions as described herein and, due to the fact that no viable microorganisms are necessary for the purpose of the present invention, it is possible to combine them with preservatives. This is very important for most applications as pharmaceutical and cosmetic products often contain preservatives in order to prevent bacterial or fungal growth in the product during repeated opening and closing of the container while the product is used up.

The skin condition(s) to be treated and/or prevented is/are preferably loss of skin barrier function, inflammatory skin conditions and/or growth of pathogenic microorganisms.

"Skin barrier" in the context of the present invention refers on the one hand to the physical and chemical barrier of the stratum corneum, which prevents substances from entering the body and protects against drying out, but on the other hand also the inductive AMP barrier, that together with other chemical properties like pH provides defense against colonization or invasion of microbial pathogens. Accordingly, a "loss of skin barrier function", which also comprises a "reduction of skin barrier function", implies that the normal or healthy skin structure and/or function is disrupted so that it can no longer provide the above mentioned protection or defense to a satisfactory degree. Preferably, however, such a disruption is not an injury such as cut or a severe burn.

"Inflammatory skin conditions" are conditions that are caused by the biological response of the skin to harmful stimuli (noxae) such as irritants or pathogenic microorganisms and usually lead to redness, swelling, heat and/or pain in the affected area. Inflammatory mediators such as inflammatory cytokines or chemokines, e.g. Interleukin 8 (IL-8), can be measured in the affected tissue to assess the inflammatory status.

"Growth of pathogenic microorganisms" such as bacteria or fungi on or in the skin can lead to infection and/or inflammation but also cause cosmetic issues such as rashes, acne or body odor. In particular, "growth of pathogenic microorganisms" refers to an increase of the amount of pathogenic microorganisms so that it exceeds a level, which is associated with a healthy microbiome, on the skin or in the skin. Especially it refers to microbial infections.

The three above described aspects are closely linked; for example, a loss of barrier function can lead to the intrusion of pathogenic microorganisms or harmful substances, which in turn cause inflammation.

In a preferred embodiment, the microorganism(s) are used as agent to
  (a) strengthen the skin barrier function, and/or
  (b) reduce transepidermal water loss, and/or
  (c) induce the expression of filaggrin, and/or
  (d) increase components related to the natural moisturizing factor, and/or
  (e) provide anti-inflammatory activity, in particular reduce and/or inhibit inflammatory parameters, and/or
  (f) provide anti-inflammatory activity induced by chemokines, and/or
  (g) provide anti-inflammatory activity induced by external noxae, such as pathogenic microorganisms, in particular *Staphylococcus aureus*, and/or air pollutants, and/or ultraviolet radiation and/or surfactants, and/or
  (h) inhibit growth of and/or invasion and/or infection by pathogenic microorganisms, in particular *Staphylococcus aureus*, and/or
  (i) induce the expression of antimicrobial peptides (AMPs), and/or
  (j) maintain and/or establish and/or restore a healthy state of the skin microbiome, and/or (k) improve the immune response of the skin.

It was found that the *Lactobacillus plantarum* strains HEAL 19 and HEAL 99 are capable to strengthen the skin barrier in different ways. For example, they can reduce transepidermal water loss (TEWL) by inducing the expression of filaggrin, which is essential for the regulation of epidermal homeostasis, in particular water retention. Furthermore, the strains have been shown to increase components related to the natural moisturizing factor, which likewise plays an important role in for appropriate stratum corneum hydration and barrier homeostasis. On the other hand, in a further aspect contributing to strengthening of the skin barrier function, the strain can induce the expression of antimicrobial peptides (AMPs) resulting in an increases protection against the invasion of pathogenic microorganisms, such as bacteria and fungi.

"Inducing" or upregulating expression of a gene in the context of the present invention, may be determined using a reference gene, e.g. a so-called house-keeping gene, the expression of which does not vary significantly in different tissues or under different conditions. Genes that are suitable as reference genes in human cells are known to the skilled person. Determining an induction or upregulation of expression using a reference gene for standardization is explained in the experimental procedures below.

It was further found that the *Lactobacillus plantarum* strains HEAL 19 and HEAL 99 can reduce inflammation mediators such as IL-8 in the skin, which are released in response to different stimuli, such as external noxae, e.g. pathogenic microorganisms or pollutants. Thus, they can reduce inflammation reactions and the associated symptoms.

In addition, the *Lactobacillus plantarum* strains HEAL 19 and HEAL 99 were shown to have an inhibitory effect on the growth of pathogenic microorganisms, in particular *Staphylococcus aureus*. They induce the expression of antimicrobial peptides (AMPs) and thus boost the immune response of the skin and are capable to maintain or establish a healthy skin microbiome. A healthy microbiome is represented by a balanced colonization of non-harmful or even beneficial (amounts of) certain microorganisms. When this balance is shifted towards a state known as microbial dysbiosis, harmful effects may ensue.

Due to the various but interconnected effects described above, the *Lactobacillus plantarum* strains HEAL 19 and HEAL 99 are useful for the prevention and/or treatment of a number of medical conditions but also improve skin appearance and other cosmetic aspects such as body odor.

In a preferred embodiment, the skin condition is selected from the group consisting of atopic dermatitis, microbial infection, dry skin, itchy skin, sensitive skin, atopic skin, inflammation of the skin, microbial dysbiosis, rosacea, psoriasis, rash and acne.

The present invention also relates to a preparation comprising or consisting of one or a mixture of two microorganism(s) selected from the group consisting of *Lactobacillus plantarum* HEAL 19 (DSM 15313) and *Lactobacillus plantarum* HEAL 99 (DSM 15316) and a carrier, wherein the preparation is a particulate preparation, preferably a granulate or a powder.

It has been found out that it is particularly advantageous to deliver the microorganism(s) for the purpose of the present invention in the form of a particulate preparation with a carrier. A particulate preparation, especially a dry granulate or powder, is more stable than e.g. a suspension and has a significantly longer shelf life when stored before application. Accordingly, no preservatives are needed to stabilize the preparation and no special storing measures such as cooling are necessary. Even over longer storage periods, the preparation shows no discoloration or other signs of deterioration. Moreover, the particulate preparation is homogenous with respect to the distribution of the microorganism(s) and no undesired effects like precipitation or agglomeration affect the homogeneity. The particulate preparation can therefore also easily and efficiently be worked into pharmaceutical or cosmetic compositions or products.

A "particulate preparation" in the context of the present invention is a preparation, which consists of distinct particles. Preferably, the particles have a homogenous size and even distribution of microorganism(s) and carrier and are dry and flowable without the tendency to form clumps. In particular, a particulate preparation may be a granulate or a powder. Such particulate preparation or, respectively, the granulate or powder, may comprise or consist of particles with an average particle size in the range of from 0.1 to 200 µM, preferably 1 to 100 µM.

A particulate preparation according to the invention can be obtained by freeze-drying, spray-drying or granulating the microorganism(s) with the carrier.

In a preferred embodiment of the preparation described above, the microorganism(s) has/have been subjected to a heat-treatment and are preferably attenuated or dead microorganism(s). However, as explained above, preferably the heat-treated microorganism(s) still have an intact physical structure.

Advantageously, the microorganisms maintain their beneficial properties with respect to the topical treatment of skin conditions during the heat-treatment. Consequently, since no viable microorganisms are necessary, the preparation can be used in pharmaceutical or cosmetic products which comprise preservatives.

The carrier used in a preparation according to the invention is a material, which is suitable to be provided in a particulate form e.g. by freeze-drying, spray-drying or granulation. It is furthermore important that the carrier is a pharmaceutically and cosmetically acceptable material.

In a preparation as described above, the carrier may be selected from the group consisting of polysaccharides, preferably inulin, starch, gummi *arabicum*, whey proteins, skim milk powders and maltodextrin as well as combinations thereof, preferably maltodextrin.

It has been found out in the context of the present invention that the ratio between the microorganism(s) and the carrier is decisive for the properties of the preparation. If too less carrier, e.g. maltodextrin, is used, the preparation typically becomes hygroscopic, which can negatively affect the stability and increase the tendency to form clumps.

In a preferred embodiment, in the preparation described above, the ratio of microorganism(s) to carrier is in the range from 1:9 to 3:7, preferably 1.5:8.5 to 2.5 to 7.5 and/or the preparation comprises 10 to 30 wt.-% microorganism(s) and 70 to 90 wt.-% of the carrier, preferably 15 to 25 wt.-% microorganism(s) and 75 to 85 wt.-% of the carrier, in each case with respect to the total weight of the preparation.

The present invention also relates to a preparation according to any of the embodiments described above for use in the treatment and/or prevention of the skin conditions by topical application. In particular, the skin condition(s) to be treated and/or prevented is/are loss of skin barrier function, inflammatory skin conditions and/or growth of pathogenic microorganisms, preferably the skin condition(s) is/are selected from the group consisting of atopic dermatitis, microbial infection, dry skin, itchy skin, sensitive skin, atopic skin, inflammation of the skin, microbial dysbiosis, rosacea, psoriasis, rash and acne.

The present invention also relates to a method for producing a preparation comprising or consisting of one or a mixture of two microorganism(s) selected from the group consisting of *Lactobacillus plantarum* HEAL 19 (DSM 15313) and *Lactobacillus plantarum* HEAL 99 (DSM 15316) and a carrier, preferably a preparation according to any of the embodiments described above, comprising the step(s):
  (i) providing one or a mixture of two microorganism(s) selected from the group consisting of *Lactobacillus plantarum* HEAL 19 (DSM 15313) and *Lactobacillus plantarum* HEAL 99 (DSM 15316);
  (ii) optionally, subjecting the microorganism(s) of step (i) to a heat-treatment, preferably at a temperature in the range of 60 to 121° C. for 1 second to 120 minutes; and
  (iii) combining the microorganism(s) from step (i) or (ii) with a carrier and further processing the combination to obtain a granulate or a powder, preferably by freeze-drying, spray-drying or granulating.

The method described above represents a highly advantageous way to process the microorganism(s) for the purpose of the present invention because the resulting preparation is very stable as described above and can be easily and efficiently worked into a wide range of pharmaceutical or cosmetic products.

According to a further aspect, the present invention also relates to a pharmaceutical or cosmetic composition or pharmaceutical or cosmetic product for topical application to the skin comprising one or a mixture of two microorganism(s) selected from the group consisting of *Lactobacillus plantarum* HEAL 19 (DSM 15313) and *Lactobacillus plantarum* HEAL 99 (DSM 15316) or comprising a preparation according to any of the embodiments described above, wherein the total amount of the microorganism(s) is sufficient for treating and/or preventing skin conditions, in particular inflammatory skin conditions, loss of skin barrier function, and/or growth of pathogenic microorganisms, preferably wherein the total amount of the microorganism(s) is in the range from 0.01 to 5% dry weight, preferably from 0.02 to 1% dry weight, such as 0.1 to 1% dry weight, in each case with respect to the total weight of the composition, and/or wherein the total amount of the microorganism(s) is at least $10^8$, preferably $5\times10^8$ cells or at least $10^{10}$ cells per gram, preferably $10^{11}$ cells per gram of the total composition (depending on the type of composition, e.g. depending on whether the composition is a semi-finished product or a final product), such as in the range from $10^8$ to $5\times10^{10}$, preferably from $10^9$ to $10'10$ cells per gram of the total composition.

It has surprisingly been found out that *Lactobacillus plantarum* HEAL 19 and *Lactobacillus plantarum* HEAL 99 are able to provide the herein described effects already at concentration as low as 0.01 or 0.02% of the dry weight of the pharmaceutical or cosmetic composition or product.

For example, a *Lactobacillus* suspension or, more preferably, a particulate preparation as described above can be used as active ingredient for various pharmaceutical or cosmetic applications, such as topical leave-on or rinse-off formulations. Compositions containing effective amounts can be useful for reducing skin sensitivity or the treatment of skin disorders like dry, itchy skin or atopic dermatitis. The compositions are suitable for continuous treatment of atopic skin as well as for the application on specific affected skin areas, like lesions, scratches or wounds. Furthermore, the compositions can be used on a daily basis for maintaining an intact barrier as well as a healthy state of the skin microbiome.

In a preferred embodiment of the pharmaceutical or cosmetic composition or product, the microorganism(s) has/have been subjected to a heat-treatment and are preferably attenuated or dead microorganisms but still having an intact physical structure. For the conditions of the heat treatment, the above defined parameters apply accordingly.

Advantageously, since the microorganisms typically maintain their beneficial properties with respect to the topical treatment of skin conditions during the heat-treatment and no viable microorganisms are required, the pharmaceutical or cosmetic products may comprise preservatives.

In a preferred embodiment, the pharmaceutical or cosmetic composition or product according to any of the embodiments described herein therefore comprises at least one preservative.

A "preservative" in the context of the present invention refers to a substance, which inhibits or suppresses microbial growth.

The invention also relates to a pharmaceutical or cosmetic composition or product as described above for use in in the treatment and/or prevention of skin conditions by topical application, in particular loss of skin barrier function, inflammatory skin conditions and/or growth of pathogenic microorganisms.

As the *Lactobacillus plantarum* strains HEAL 19 and HEAL 99 provide the above described effects a) to k) when topically applied to the skin, compositions and products comprising an effective amount of one or both strains are effective to treat and/or prevent a number of skin conditions and improve the appearance of the skin as described above.

The compositions and products according to the invention are intended for topical application on the skin and thus are preferably in a formulation suitable for topical application on the skin. Such formulations may be leave-on or rinse-off formulations.

In further preferred embodiment, the pharmaceutical or cosmetic composition or product as described above is selected from the group consisting of oil in water or water in oil emulsion, ointment, crème, lotion and gel.

The compositions and products may comprise further ingredients that provide suitable properties for application on the skin. Preferred is therefore a pharmaceutical or cosmetic composition or product further comprising one or more component(s) selected from the group consisting of carriers, excipients and further active ingredients, preferably selected from maltodextrin, inulin, emollients and plant oils.

The present invention also relates to a method for producing a pharmaceutical or cosmetic composition or product, preferably a pharmaceutical or cosmetic composition or product according to any of the embodiments described herein, comprising the steps:
  (i) providing one or a mixture of two microorganism(s) selected from the group consisting of *Lactobacillus plantarum* HEAL 19 (DSM 15313) and *Lactobacillus plantarum* HEAL 99 (DSM 15316), preferably wherein the microorganism(s) has/have been subjected to a heat-treatment and are preferably attenuated or dead microorganisms having an intact physical structure, or providing a preparation according to any of the embodiments described above or a preparation produced by a method as described above, and
  (ii) combining the microorganism(s) or the preparation of step (i) with one or more substances selected from carriers, excipients and further active ingredients to obtain a pharmaceutical or cosmetic composition or product.

In a preferred embodiment of the method, in step (ii) at least one preservative is combined with the microorganism(s) or the preparation of step (i).

According to the present invention, the plant oils may be selected from the group consisting of Argan oil, Chokeberry (seed) oil, Avocado oil, Peach (pits) oil, Canola oil, Nigella oil, Pumpkin (pumpkin seed) oil, Wild rose (seeds) oil, Pomegranate seeds oil, Jojoba (liquid wax) oil, Cocoa/cocoa butter, Wheat sprout oil, Coconut/coconut butter, Safflower oil, Corn oil, Camelina oil, Flax seed oil, Macadamia oil, Raspberries seeds oil, Meadowfoam seeds oil, *Passiflora* seeds oil, Almond oil, Neem oil, Moringa oil, Borago oil, Olive oil, Peanuts oil, Hazelnuts oil, Walnut oil, Palm oil, Papaya seeds oil, Parsley seeds oil, Seabuckthorn oil, Castor oil, Rice oil, Sesame oil, Shea butter/karité butter, Sunflower oil, Soybean oil, Tamanu oil, Evening primrose oil, Grape seeds oil, Cranberry seeds oil.

According to the present invention, further suitable oil bodies may be selected from the group consisting of Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.), aliphatic or naphthenic hydrocarbons, such as, for example, squalane, squalene or dialkylcyclohexanes, and/or mineral oils.

In the compositions and products according to the invention, preferably, the *Lactobacillus plantarum* strains HEAL19 and HEAL99 are used in combination with one or more (further) substances for preventing, reducing or alleviating dry and/or itchy skin condition(s) and/or one or more skin irritation-reducing agents, in particular one or more substances selected from the group consisting of anti-inflammatory agents, physiological cooling agents and compounds that alleviate reddening, preferably wherein the one or more additional substances is/are selected from the group consisting of:

(i) anti-itch compounds, (ii) steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone, (iii) non-steroidal anti-inflammatory substances, in particular oxicams such as piroxicam or tenoxicam, salicylates such as aspirin, disalcid, solprin or fendosal, acetic acid derivatives such as diclofenac, fenclofenac, indomethacin, sulindac, tolmetin or clindanac, fenamates such as mefenamic, meclofenamic, flufenamic or niflumic, propionic acid derivatives such as ibuprofen, naproxen or benoxaprofen, pyrazoles such as phenylbutazone, oxyphenylbutazone, febrazone or azapropazone, (iv) natural or naturally occuring anti-inflammatory substances or substances that alleviate reddening and/or itching, in particular extracts or fractions from camomile, Aloe vera, *Commiphora* species, *Rubia* species, willow, willow-herb, oats, calendula, arnica, St John's wort, honeysuckle, rosemary, *Passiflora incarnata*, witch hazel, ginger or *Echinacea*, or single active compounds thereof, (v) alpha-bisabolol, apigenin, apigenin-7-glucoside, gingerols, shogaols, gingerdiols, dehydrogingerdiones, paradols, natural avenanthramides, non-natural avenanthramides, preferably dihydroavenanthramide D, boswellic acid, phytosterols, glycyrrhizin, glabridin and licochalcone A, preferably in the form of pure substances, (vi) skin care agents, preferably skin moisture retention regulators or skin repair agents, preferably selected from the group consisting of sodium lactate, urea and derivatives, glycerol, propylene glycol, 1,2-pentanediol, 1,2-hexanediol and 1,2-octanediol, collagen, elastin or hyaluronic acid, diacyl adipates, petrolatum, urocanic acid, lecithin, allantoin, panthenol, phytantriol, lycopene, (pseudo-)ceramides (preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide), glycosphingolipids, cholesterol, phytosterols, chitosan, chondroitin sulfate, lanolin, lanolin esters, amino acids, vitamin E and derivatives (preferably tocopherol, tocopheryl acetate), alpha-hydroxy acids (preferably citric acid, lactic acid, malic acid) and derivatives thereof, mono-, di- and oligosaccharides, preferably glucose, galactose, fructose, mannose, laevulose and lactose, polysugars, such as β-glucans, in particular 1,3-1,4-β-glucan from oats, alpha-hydroxyfatty acids, triterpenic acids, such as betulic acid or ursolic acid, and algae extracts or single active compounds thereof, (vii) physiological cooling agents, preferably selected from the group consisting of menthone glycerol acetal, menthyl lactate preferably 1-menthyl lactate, in particular 1-menthyl 1-lactate), menthyl ethyl oxamate, substituted menthyl-3-carboxylic acid amides (e.g. menthyl-3-carboxylic acid N-ethylamide, $N^\alpha$-(L-menthanecarbonyl)glycine ethyl ester, 2-isopropyl-N-2,3-trimethylbutanamide, substituted cyclohexanecarboxylic acid amides, 3-menthoxypropane-1,2-diol, 2-hydroxyethyl menthyl carbonate, 2-hydroxypropyl menthyl carbonate, N-acetylglycine menthyl ester, isopulegol, menthyl hydroxycarboxylic acid esters (e.g. menthyl 3-hydroxybutyrate), monomenthyl succinate, monomenthyl glutarate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl 3,6-di- and -trioxaalkanoates, 3-menthyl methoxyacetate and icilin, and (viii) histamine receptor antagonists, serine protease inhibitors, TRPV1 antagonists, NK1 antagonsists, cannabinoid receptor agonists and TRPV3 antagonists.

According to a further aspect, the present invention also relates to a cosmetic use of a microorganism or mixture comprising or consisting of two microorganisms for topical application on the skin, in particular to improve the appearance of the skin and/or prevent body odor, wherein the microorganism(s) is/are selected from the group consisting of *Lactobacillus plantarum* HEAL 19 (DSM 15313) and *Lactobacillus plantarum* HEAL 99 (DSM 15316), preferably wherein the microorganism(s) has/have been subjected to a heat-treatment and/or are attenuated or dead microorganisms having an intact physical structure.

A "cosmetic use" is a non-therapeutic use, i.e. a use on skin, the appearance of which is affected by e.g. irritation, redness, dryness, flaking, rash, signs of ageing or light cases of acne, which represent a cosmetic issue or a slight discomfort but would not be characterized as pathologic. A further "cosmetic use" is the prevention or reduction of body odor, which is associated with the growth of certain microorganism on the skin, which cause bad smell but do not represent an imminent danger to the affected person's health.

Accordingly, the cosmetic use described above is preferably for reducing or preventing skin irritation, dry skin, rash, acne, body odor and/or skin aging.

In the cosmetic use according to the invention, the microorganism(s) are used as agent to (a) strengthen the skin barrier function, and/or
(b) reduce transepidermal water loss, and/or
(c) induce the expression of filaggrin, and/or
(d) increase components related to the natural moisturizing factor, and/or
(e) provide anti-inflammatory activity, in particular reduce and/or inhibit inflammatory parameters, and/or
(f) provide anti-inflammatory activity induced by chemokines, and/or
(g) provide anti-inflammatory activity induced by external noxae, such as pathogenic microorganisms, in particular *Staphylococcus aureus*, and/or air pollutants, and/or ultraviolet radiation and/or surfactants and/or
(h) inhibit growth of and/or invasion and/or infection by pathogenic microorganisms, in particular *Staphylococcus aureus*, and/or
(i) induce the expression of antimicrobial peptides (AMPs), and/or
(j) maintain and/or establish and/or restore a healthy state of the skin microbiome, and/or
(k) improve the immune response of the skin.

The effects described under items (a) to (k) and explained in more detail further above, also represent a suitable combination to address a number of solely cosmetic issues. For example, loss of skin barrier function may lead to increased transepidermal water loss, which results in dry skin that shown signs of irritation such as redness or flaking and thus affects the appearance of the skin. Upregulation of filaggrin and increase of components related to the natural moisturizing factor prevent or alleviate such issues. Anti-inflammatory activity reduces sings of swelling or redness caused by the skins reaction to certain stimuli, which affects the appearance of the skin but does not represent a pathological condition. Inhibiting the growth of pathogenic microorganisms e.g. by inducing the expression of AMPs can resolve mild cases of acne or prevent and reduce body odor.

In a preferred embodiment of the cosmetic use described above, the microorganism(s) are used in the form of a preparation according to any of the embodiments described above.

In a further aspect, the present invention also relates to a cosmetic method to improve the appearance of the skin and/or prevent body odor, in particular to reduce or prevent skin irritation, dry skin, rash, acne body odor and/or skin aging, comprising the step i) applying a microorganism or a mixture comprising or consisting of two microorganisms topically to the skin, wherein the microorganism(s) is/are selected from the group consisting of *Lactobacillus plantarum* HEAL 19 (DSM 15313) and *Lactobacillus plantarum* HEAL 99 (DSM 15316), or applying a preparation or a cosmetic composition or product as described above to the skin, preferably wherein the microorganism(s) has/have been subjected to a heat-treatment and/or are attenuated or dead microorganisms having an intact physical structure.

A "cosmetic method" is a non-therapeutic method to resolve cosmetic issues but not to treat pathologic conditions as explained in more detail in the context of the cosmetic use above. In a cosmetic method according to the present invention, the microorganism(s) act as agent to provide the effects described above under items (a) to (k) and are thus able to resolve a number of cosmetic issues as explained in the context of the cosmetic use above.

SHORT DESCRIPTION OF THE FIGURES

FIG. 1 shows the induction of antimicrobial peptides by *L. plantarum* HEAL 19 in HaCaT keratinocytes. Significantly induced genes are β-Defensin 3, β-Defensin 4, Peptidase inhibitor 3, RNase 7, Psoriasin, Lactotransferrin and Secretory leukocyte peptidase inhibitor. Gene expression of antimicrobial peptides in HaCaT keratinocytes was measured after 24 h treatment with 0.05% *L. plantarum* HEAL 19 using gene arrays; induction was defined as a calculated RQ-value of >2.

FIG. 2 shows the concentration dependent induction of β-Defensin 3 by *L. plantarum* HEAL 19 in HaCaT keratinocytes. HaCaT keratinocytes were treated for 24 h with various concentrations of *L. plantarum* HEAL 19. This results in calculated RQ-values from 243.6 (by 0.1% *L. plantarum* HEAL 19) to 2.3 (0.0125% *L. plantarum* HEAL 19).

FIG. 3 shows various inductions of AMP coding genes after 24 h treatment. RNase 7, β-Defensin 3 Peptidase inhibitor 3, Phospholipase A2, and Secretory leukocyte peptidase inhibitor are induced concentration dependently (0.1 and 0.05% were tested) with *L. plantarum* HEAL 99.

FIG. 4 shows the anti-inflammatory effect of *L. plantarum* HEAL 19 and 99 and dexamethasone, which was included as a positive control. The confluent HaCaT keratinocytes were pre-treated with the test material *L. plantarum* HEAL 99 with 0.1 mg/mL, *L. plantarum* HEAL 19 with 0.25 mg/mL and dexamethasone in 30 µM. After 48 hours incubation keratinocytes were stimulated using 30 ng/mL of pro-inflammatory IL-1alpha for 8 hours. The subsequent Interleukin-8 release from HaCaT keratinocytes due to IL-1alpha stimulation after pre-treatment with *L. plantarum* HEAL 19 and HEAL 99 was measured in the cell culture medium using ELISA. Comparison is shown to positive control dexamethasone and not pre-treated keratinocytes (IL-1alpha control).

Figure 11:
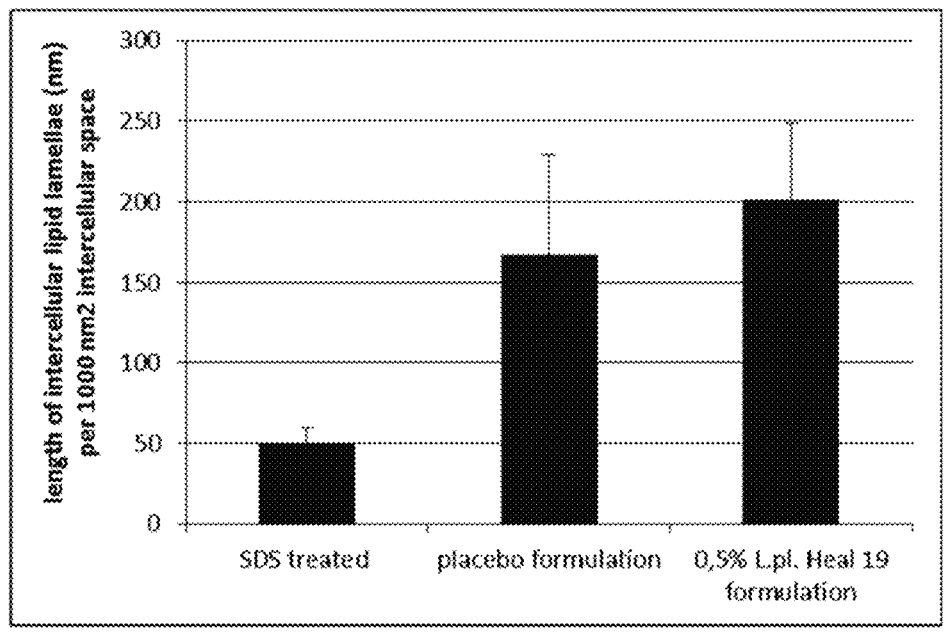

FIG. 11 shows the length of intercellular lipid lamellae (nm) per 1000 nm2 intercellular space measured in 3D epidermis model systems for dry skin. Lamellae were disturbed due to SDS treatment. Skin repair performance was determined by transmission electron microscopy (TEM) after treatment with 0.5% *L. plantarum* HEAL 19 in a skin care formulation.

Figure 12:
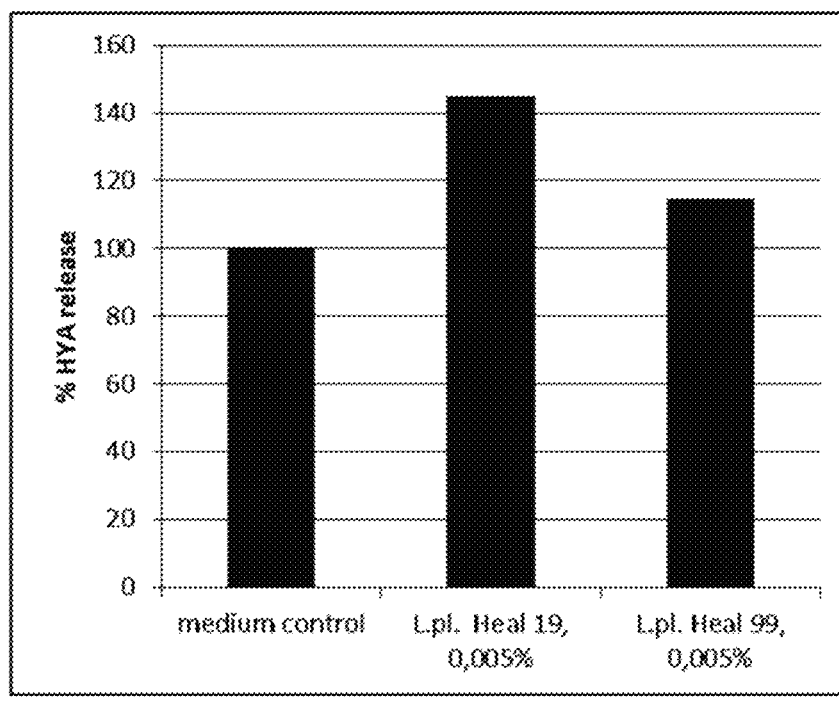

FIG. 12 shows hyaluronic acid release of HEPKp 3 dimensional skin models (axis of ordinates) after treatment with *L. plantarum* HEAL 19 and HEAL 99. Comparison is shown to a negative control including only the cell culture medium (medium control), x-axis.

Figure 13:
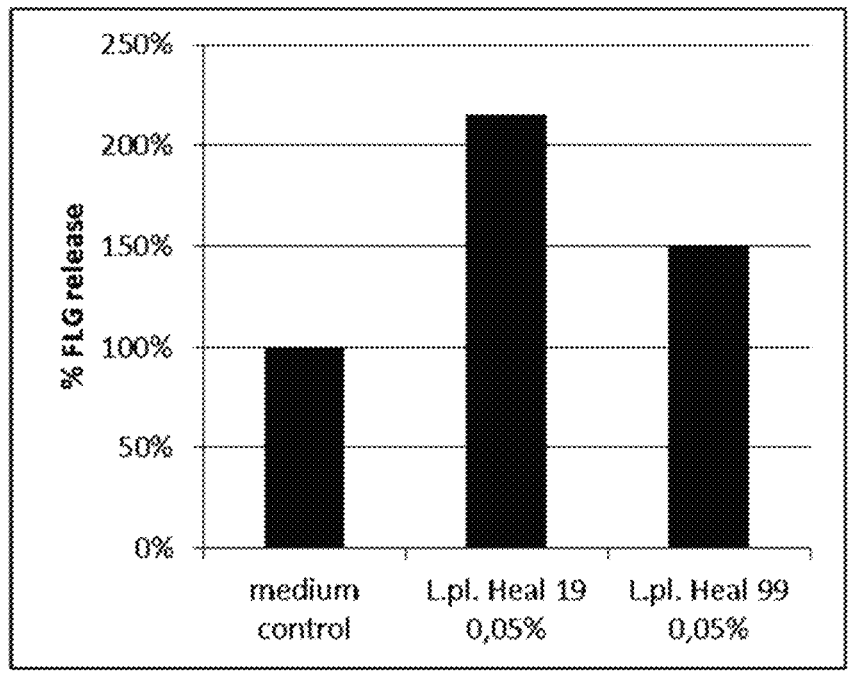

FIG. 13 shows the filaggrin release from HEPKp 3 D skin models (axis of ordinates) after treatment with *L. plantarum* HEAL 19 and HEAL 99. Comparison is shown to a negative control including only the cell culture medium (medium control), x-axis.

Figure 14:
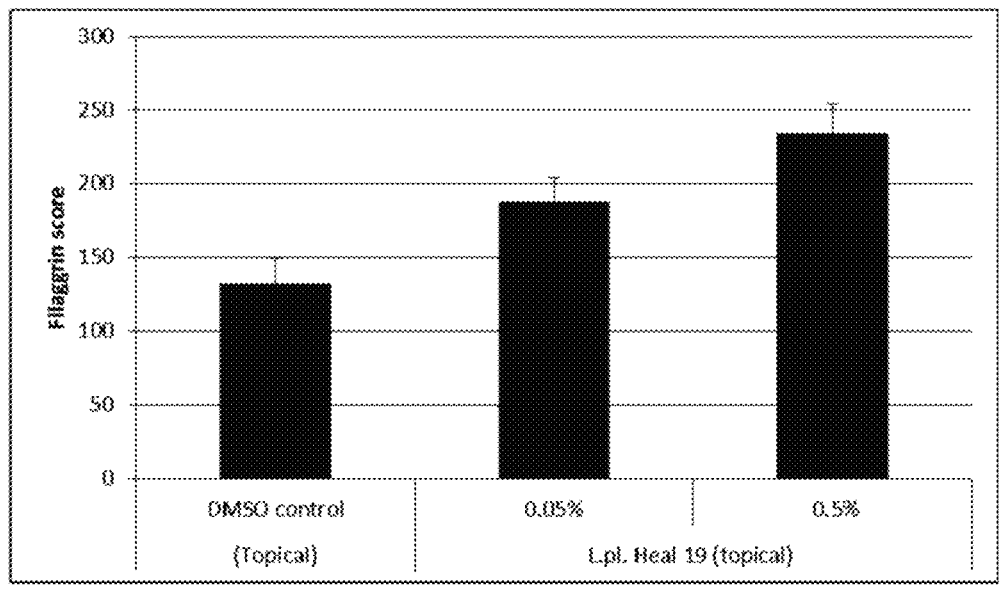

FIG. 14 shows the filaggrin contents in ex vivo human skin models after treatment with *L. plantarum* HEAL 19 at two different concentrations. Comparison is shown to a negative control including only the vehicle (DMSO).

Figure 15:
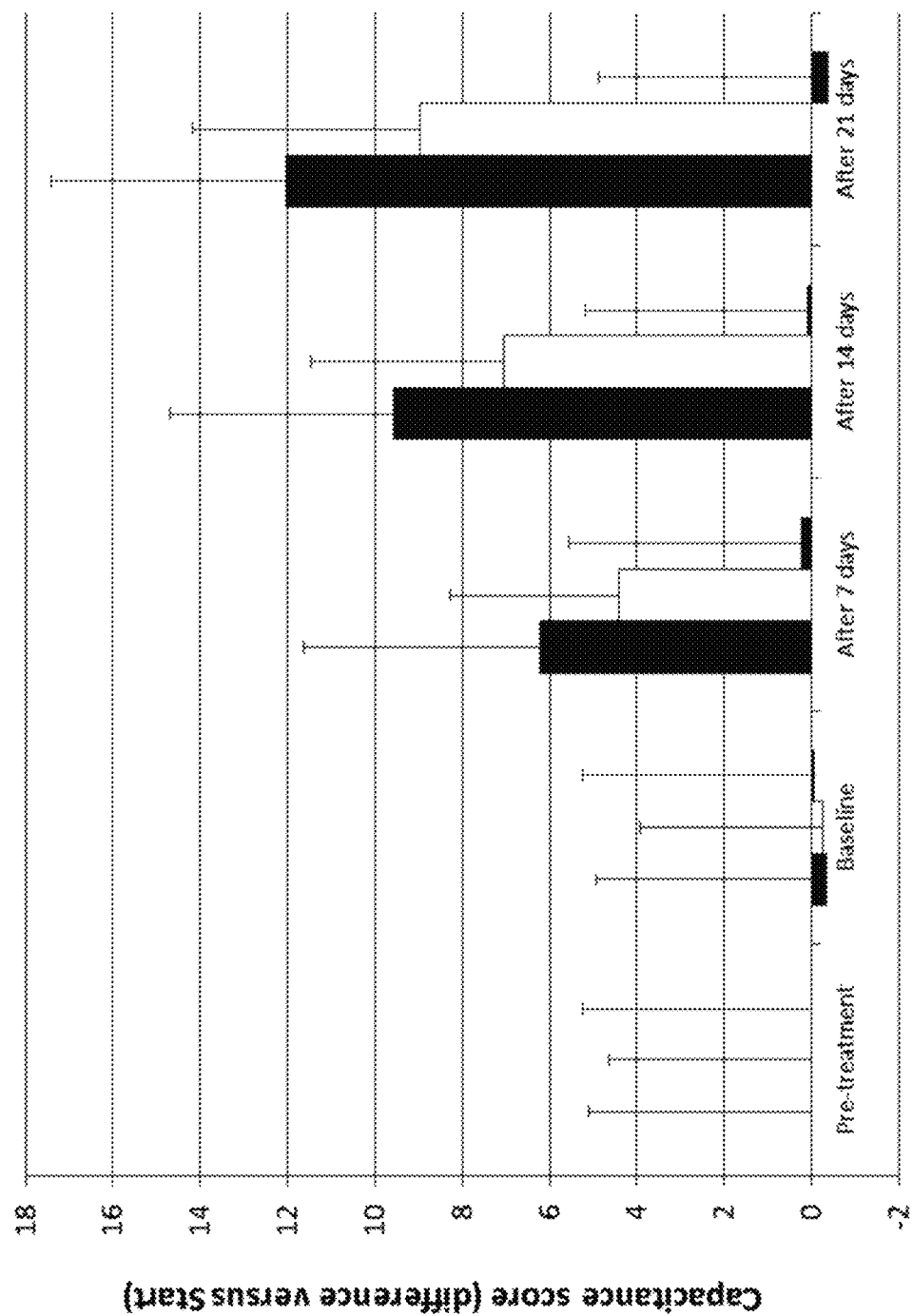

FIG. 15 shows the water content as determined by capacitance in in vivo human skin after treatment with *L. plantarum* HEAL 19 at 1% concentration in a cosmetic cream. Grey shaded bars represent cream with *L. plantarum* HEAL 19, white bars represent placebo cream, black bars indicate no treatment.

Figure 16:
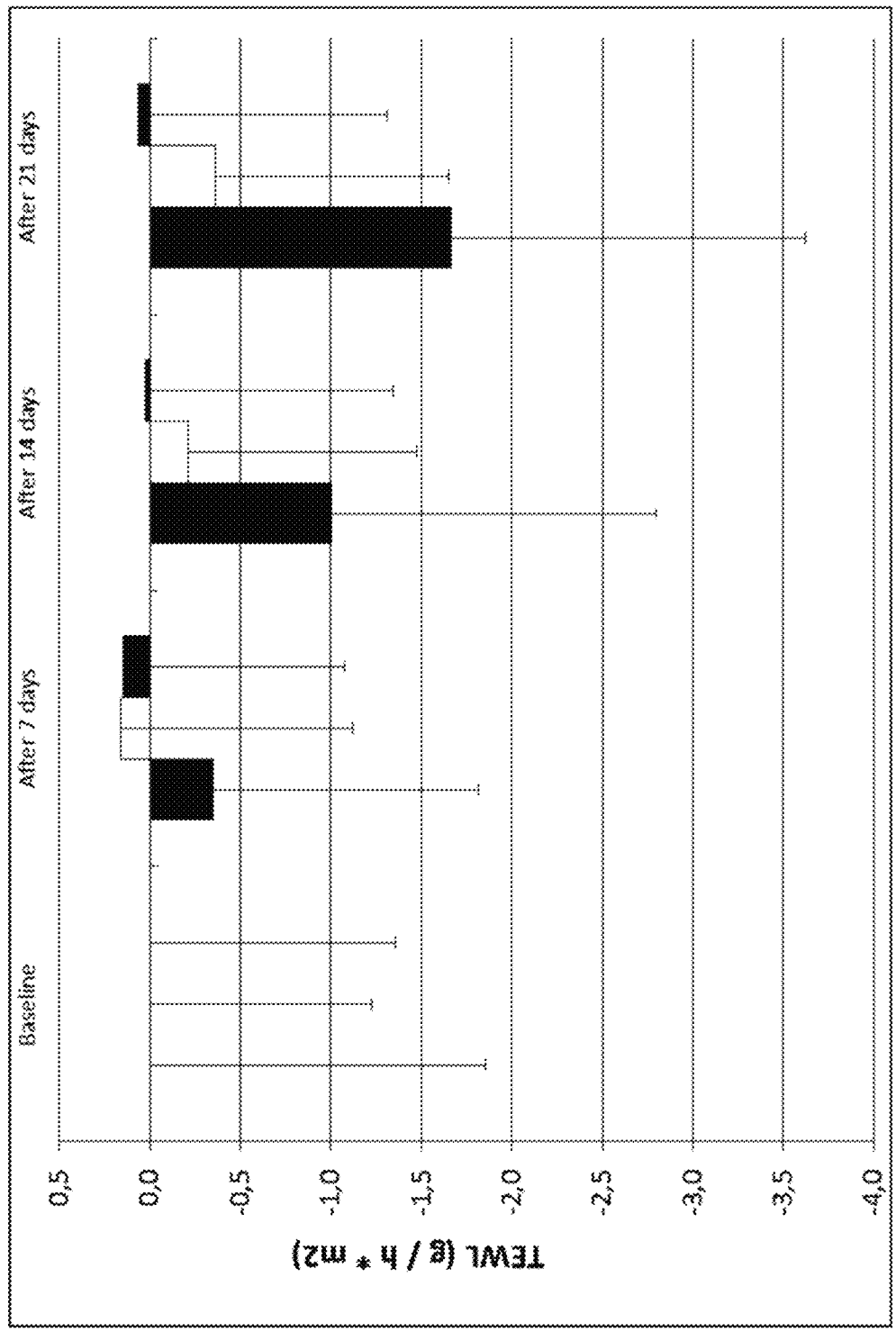

FIG. 16 shows the skin barrier strength as determined by transepidermal water loss (TEWL) in in vivo human skin after treatment with *L. plantarum* HEAL 19 at 1% concentration in a cosmetic cream. Grey shaded bars represent cream with *L. plantarum* HEAL 19, white bars represent placebo cream, black bars indicate no treatment.

Figure 17:
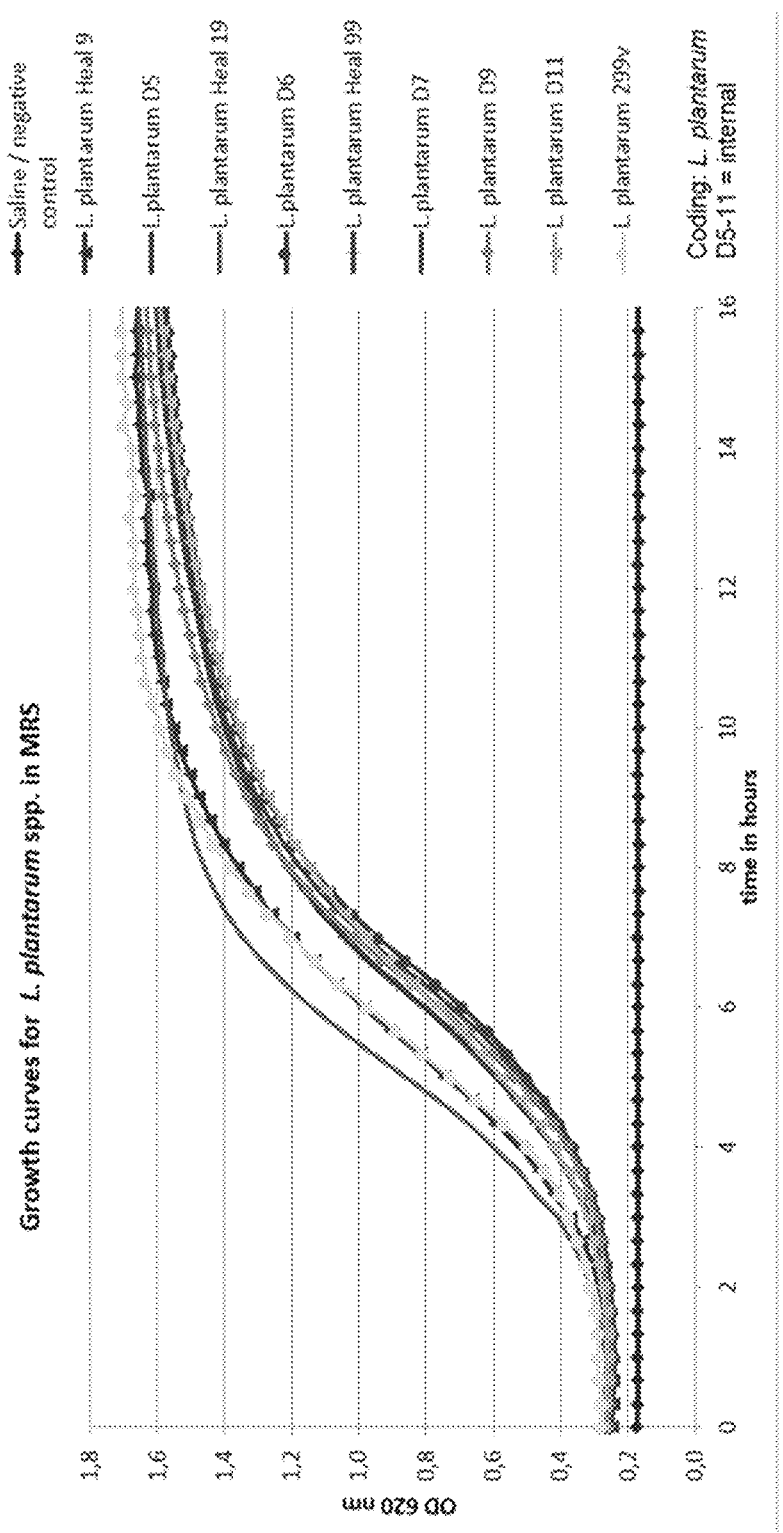

FIG. 17 shows growth curves for *L. plantarum* spp. in MRS medium over 16 h; start-OD=0.1; average of 3 cavities.

The invention is further illustrated by the examples below, which are not to be understood as limiting for the scope.

The following experimental procedures were used in the examples:

Preparation of Heat-Treated Lactobacilli Suspensions

The growth of the *L. plantarum* strains HEAL 19 and HEAL 99 can be obtained in various culture media. The carbon source can be glucose or starch. Meat extract, yeast extract, peptone or protease peptone (vegetable) etc. can be used as nitrogen source. The pH of the culture medium should be about 6. The culture temperature is variable, but preferably 37° C. Culture duration may be about 8 to 24 h. Shaking or aerated shaking can be added.

After cultivation, a washing process can be added. It can be done as follows. Cells can first be collected by centrifugation, supernatant decanted and cell pellets suspended with liquid PBS, cell culture medium or purified water. The described procedure can be repeated if needed.

Heat-treatment of the Lactobacilli suspension can be done before or after a washing procedure. It can be achieved by ultrasound, UV-irradiation or heat, whereas heat-treatment is preferable. It can be performed with temperatures from 60° C. to 121° C. For temperatures above 100° C., an autoclave may be used. Heat-treatment durations can range from 1 s to 120 min, such as from 20 s to 120 min. Heat-treatment between 70 and 100° C. for 20 s to 15 min using an industrial pasteurizer is preferable. Optional further processing for the heat-treated Lactobacilli can include freeze-drying, spray-drying, granulating etc. This can serve the purpose of improving applicability and/or stability of the product itself.

The final product can be a powder, granulate, suspension or solution and is defined to be applied in cosmetic compositions in a concentration of 0.001 to 10% w/v. This relates to a concentration of $1\times10^7$-$1\times10^{11}$ cells/mL cosmetic formulation. More preferably, the final product is applied in a concentration of 0.01 to 5% w/v, and even more preferably, in 0.02 to 1% w/v, such as from, 0.1 to 1% w/v.

Effects of *Lactobacillus* Strains on AMP Gene Expression in Keratinocytes Grown as Mono-Layer AMP inductions were measured with real time PCR analysis using Taq-Man® Array fast 96-well plates.

HaCaT keratinocytes were cultivated in EpiLife medium, cascade Biologics, Gibco, incl. HKGS, Gibco, life technologies. Test substances were diluted in equal medium and added in a volume of 2 mL per well on 6-well plates. All samples are tested on 100% confluent cells incubated at 37° C., 5% CO2. After 24 h incubation time all samples were removed and cells washed twice with Dulbecco's Phosphate Buffered Saline with Ca and Mg, Capricorn. RNA isolation was performed using RNeasy® Mini Kit, Qiagen. The procedure has been done as describes in the RNeasy Mini Handbook.

Cells were lysed and precipitated with ethanol, the homogenate was washed three times using the spin column and the mRNA was eluated with purified water. Depending on the sample the procedure was slightly adjusted.

RNA concentration was measured using μCuvetteG 1.0 and BioPhotometer, Eppendorf by measuring the absorption at 260 nm. Control values, like E260/280 or E260/230 were calculated simultaneously. Transcription was done with a minimum of 0.5-1 μg RNA per sample.

Reverse transcription was done using high capacity RNA-to-cDNA Kit, Applied Biosystems. The procedure was based on the provided protocol. All samples were incubated in a PCR Thermocycler, Biometra running 60 min at 37° C. for reverse transcription, followed by 5 min at 95° C. (enzyme inactivation) and holding temperature at 4° C. in reaction room.

Quantitative Real-Time PCR was done using StepOne Plus Fast Real Time PCR Instrument, Applied Biosystems. Initial steps of the RT-PCR included a first heating phase holding for 20 s at 95° C., followed by 40 cycles of cDNA denaturation for 3 s at 95° C. and annealing/elongation at 60° C. for 30 s.

Analysis was done by 2-ACT Method—in detail:
1. Standardization of Ct values with reference-gen (HPRT)

$$\Delta C_T value_{gene} = C_T value_{gene} - C_T value_{Referencegene\ (HPRT)}$$

2. Subtraction of ACT-value of control sample (untreated) and ACT-value (treated)

$$\Delta\Delta C_T value_{gene} = \Delta C_T value_{treated} - \Delta C_T value_{control}$$

3. Calculation of RQ-Ratio (relative quantification-value)

$$RQ\text{-value} = 2^{-\Delta\Delta C_T}$$

A RQ-Value of >2 was defined as relevant induction of a gene.

Anti-Inflammatory Effects of *Lactobacillus plantarum* HEAL 19 and HEAL 99

HaCaT keratinocytes were cultivated in 96-well plates using RPMI-A, medium sterile filtered with L-Glutamine, Capricorn, supplemented with 10% fetal calf serum (FCS), Capricorn. The plates were incubated at 37° C. and 5% CO2. After 24 hours starvation with cell culture medium (RPMI, 1% FCS) the cells were washed once. The anti-inflammatory substances/inactivated bacteria suspensions were suspended in starvation medium, applied and incubated for 24/48 h with parameters described above. Dexamethasone in a concentration of 10 μM was used as positive control. To remove bacterial cells after pre-incubation all wells were washed with cell culture medium three times. IL-1alpha, Gibco, life technologies was dissolved in H$_2$Odest, diluted in starvation medium and pipetted to wells, preferably at a concentration of 30 ng/mL. Alternatively, a heat inactivated *Staphylococcus aureus* (DSM799) suspension was used as pro-inflammatory agent in a concentration of 0.1 mg/mL-1 mg/mL dry mass. After 8 h incubation the supernatants were separated. All samples were stored at −80° C. until further analyses.

IL-8 concentrations were measured with Human CXCL8/IL-8, DuoSet ELISA, Development Systems, R&D Systems. The experimental procedure was performed as described in the provided protocol.

After calculating means of the duplicate/triplicate values and subtraction of the average zero standard optical density the calculation was done using four parameter logistic curve-fit for creating standard curves.

Induction of Hyaluronic Acid

Human epidermal keratinocyte progenitors (HEPKp) generated 3d human skin models were cultivated and systemically treated with test substances. Briefly, defined concentrations of test substances were added to cell culture medium and each skin model was treated in cell culture dishes for up to 9 days at 37° C. and 5% CO$_2$. After the treatment, collected supernatants were stored at −80° C. until further analyses. Viability of the cells was controlled by MTT standard method.

Hyaluronic acid concentrations were measured by TECO-medical hyaluronic acid plus ELISA. The experimental procedure was performed as described in the provided protocol.

Antimicrobial Effects of the *Lactobacillus* Strains

Growth curves of various bacteria were measured photometrically at 620 nm.

Inhibition of *Staphylococcus aureus:*

96-well MTP were prepared according to DIN58940-8 with autoclaved CASO medium (MERCK 1.05459) and test substances dissolved in DMSO or distilled water. The relevant wells were inoculated with *S. aureus* (DSM799/ATCC6538) using stock cultures maintained in 10% glycerin at −20° C. An inoculum of 1-6×10$^6$ cfu was added per well. Test substances were analyzed using three or four replicate wells during incubation at 37° C. for 16 hours. Growth curves were determined in each well via absorption at 620 nm using a Sunrise Photometer (Tecan, Austria) and Magellan Software. A concentration of 125 ppm farnesol and 4 ppm triclosan was used as positive control for growth inhibition, both pre-dissolved in DMSO (Merck 802912).

For calculation, averages of detected absorptions were calculated and normalized with blank values. These OD values were plotted in function of time for graphical presentation.

Induction of Moisturizing Factor Filaggrin in 3D Skin Models

Three dimensional skin models derived from human epidermal keratinocyte progenitors (HEPKp) and were systemically treated with test substances in CnT-PR-3D medium for 4 to 9 days. The filaggrin release was detected in the media by ELISA, Enzyme-linked Immunosorbent Assay Kit for filaggrin, Cloud-Clone Corp.

Barrier Improving Efficacy on SDS Damaged 3D Skin Models for Dry Skin

For this purpose an in vitro study was performed on a 3D epidermis model system for dry skin. The model system consisted of 14 day-old, mature epidermis cell cultures which had a disturbed epidermal skin barrier due to SDS treatment. Disturbance of the epidermal barrier was measured as loss of intercellular lipid lamellae. The skin repair performance was determined by transmission electron microscopy (TEM) after treatment with *L. plantarum* HEAL 19 formulated in a cosmetic emulsion or placebo emulsion and then further cultivated to observe reformation of intercellular lipid lamellae.

Ex Vivo Studies

Ex vivo trials were done by Cutech Srl, Italy. Effects of described *Lactobacillus* strains on various parameters were analyzed in ex vivo skin models. Human skin from abdominal plastic surgery was used. Applications of heat inactivated bacteria suspensions were done systemically or topically, in formulation or solved in cell culture medium Tape stripping may be used. Concentrations and incubation times may vary.

All data were processed in terms of mean, standard deviation and standard error of mean (SEM) for each treatment.

Epidermal Filaggrin, Involucrin and Cytokeratin 14

For analyses, the models were immune-stained with the selected antibody filaggrin rabbit polyclonal [H-300], involucrin mouse monoclonal (SY5) and/or cytokeratin 14 (CK14) rabbit monoclonal (EPR17350). The amount of the antigen present in each slide was evaluated by estimating the intensity and the distribution of red dye within the epidermis. The obtained data were normalized for the length of the basal lamina.

Skin Barrier Integrity (Rhodamine B)

Ex vivo skin models have been treated topically with the *L. plantarum* strains before the application of the diesel particulate (i.e. 1650b). All skin samples have been incubated at 35° C., 5% CO2 and environmental humidity. At the end of the experimental phase the skin samples have been harvested stained with Rhodaminde B, cryo-fixed and cut at the cryostat for consequent image acquisition and analysis. The analysis of Rhodamine B fluorescence has been performed within two sections of the epidermis area for each skin model. Images have been analyzed by evaluating the fluorescence through Image-J application (NIH, USA).

Anti-Inflammatory Effects

Above described ex vivo human skin models have been used to verify the anti-inflammatory potential of the *L. plantarum* strains. The models were treatment with a *L. plantarum* HEAL 19 cosmetic emulsion followed by the application of the external noxious agent and pollutant 1650b, simulating air pollution. At a selected endpoint, the organ cell culture medium has been withdrawn from wells and analyzed for IL-8 using Deluxe set Human IL-8 of Biolegend®, Inc.

In Vivo Studies

In vivo trials were done at Kosmoscience Ciência & Tecnologia Cosmética Ltda, Brazil. They assessed relevant skin parameters after application of a cosmetic o/w formulation containing *L. plantarum* HEAL 19 lyophilisate.

The o/w emulsion had the following composition:

| Phase | Ingredients | INCI | Placebo % | Active % |
|---|---|---|---|---|
| A | Dracorin GOC | Glyceryl Oleate Citrate, Caprylic/Capric/ Triglyceride | 2 | 2 |
| | LanetteO | Cetearyl Alcohol | 3 | 3 |
| | PCL liquid 100 | Cetearyl Ethylhexanoate | 2.5 | 2.5 |
| | Dragoxat 89 | Ethylhexyl Isononanoate | 2.2 | 2.2 |
| | Xiameter 200 Fluid 350 CS | Dimethicone | 0.3 | 0.3 |
| B | Carbopol EDT 2020 | Aerylates/C10-30 alkyl acrylate Crosspolymer | 0.2 | 0.2 |
| | Keltrol CG | Xanthan Gum | 0.2 | 0.2 |
| C | Water | | ad 100 | ad 100 |
| | SymSave H | Hydroxyacetophenone | 0.5 | 0.5 |
| | 2-Phenoxyethanol | Phenoxyethanol | 0.5 | 0.5 |
| | EDTA | disodium edta | 0.1 | 0.1 |
| D | NaOH 10% | | 0.2 | 0.2 |
| E | *L. plantarum* HEAL19 | | — | 1.0 |
| | Total = | | 100.00 | 100.00 |
| | pH | | 5.3 | 5.3 |

Twenty two subjects with extra dry skin participated in the study. Topical application of the emulsion was done twice-daily on the inner forearm. Measurements took place at day 0, 7, 14 and 21.

Skin Hydration by Corneometry

The measurement of capacitance was performed using a Corneometer® 825 probe coupled to a Multi Probe Adapter, MPA 5 (CKeletronics, Germany). Variation of the Capacitance and the skin hydration provided by the *L. plantarum* HEAL 19 formulation in relation to the placebo was calculated.

Effectiveness of the Skin Barrier by Evaporimetry

Transepidermal water loss (TEWL) was measured using a Tewameter® 300 probe coupled to a Multi Probe Adapter, MPA 5 (CKeletronics, Germany). Variation of the TEWL values and the cutaneous barrier fortification provided by the *L. plantarum* HEAL 19 formulation in relation to the placebo was calculated. Fortification of the skin barrier can be observed as decrease in the TEWL value.

The following results demonstrate the efficiency of the present invention. Single experiments should illustrate but not limit effects of the invention.

Example 1: AMP Gene Expression in HaCa Keratinocytes

*L. plantarum* HEAL 19 induces the release of a wide range of antimicrobial peptides in human keratinocytes. All these peptides together represent a complex defense system of the human skin. Defensins for instance, that are able to kill Gram positive bacteria, were upregulated. In sum, the upregulated peptides are effective against a broad spectrum of potentially pathogenic Gram positive and Gram negative bacteria, fungi, eukaryotic parasites and/or viruses.

Figure 1:
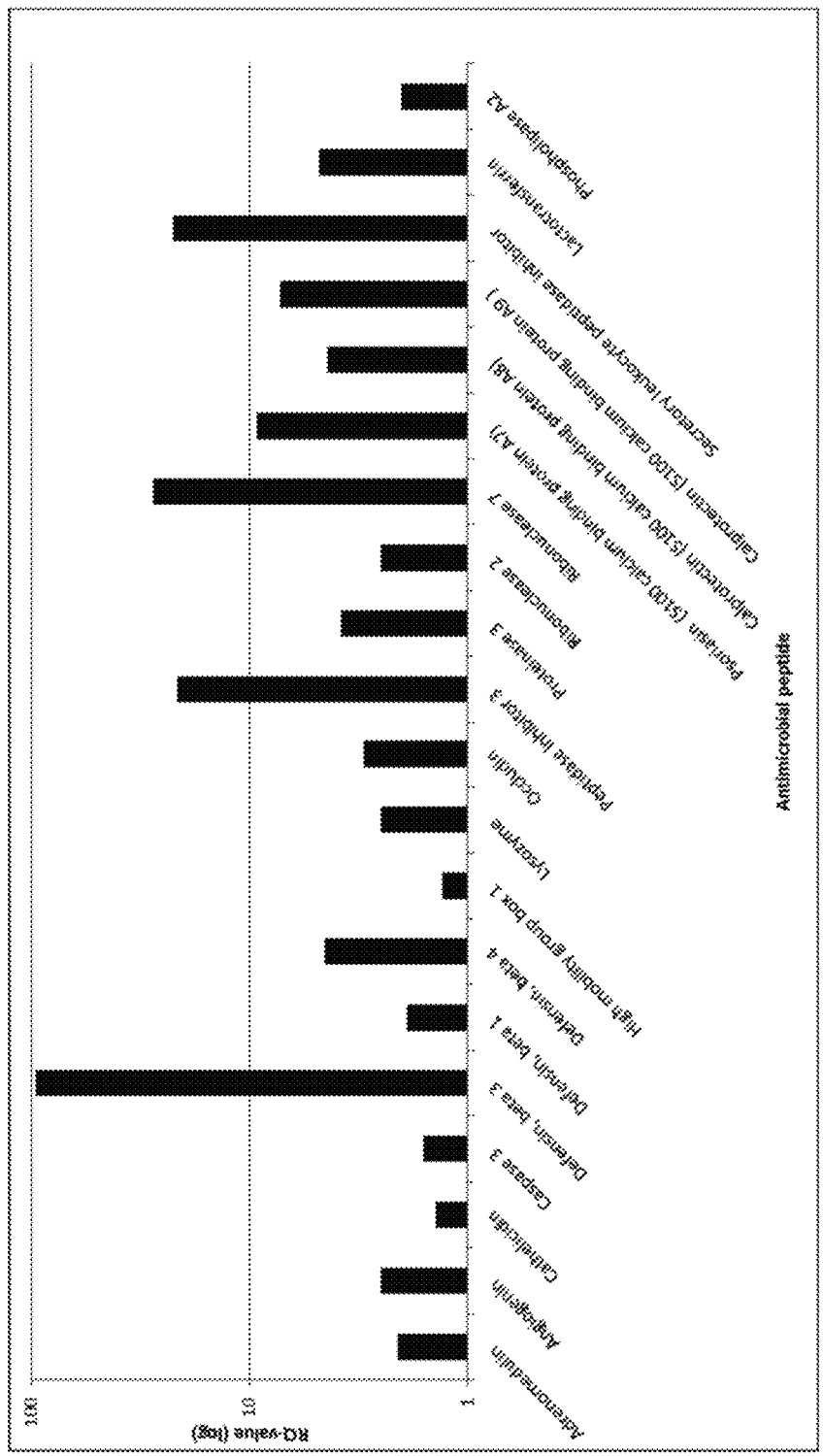

FIG. 1 shows gene expression of antimicrobial peptides in HaCaT keratinocytes after 24 h treatment with 0.05% *L. plantarum* HEAL 19. The gene expression has been measured using gene arrays; induction was defined as a calculated RQ-value of >2.

Results demonstrate that important AMPs like β-Defensin 1, 3 or 4 and/or Psoriasin and/or Calprotectin are induced by the treatment with *L. plantarum* HEAL 19. This treatment results in higher expression of AMPs in human skin, which relates to a stronger first defense line in human skin and thereby supports the skin barrier. Furthermore, the induced expression of β-Defensin or Cathelicidin can balance the AMP fingerprint in diseases such as in atopic dermatitis. Thus, the skin microbiome can be restored, maintained and/or improved by treatment of *L. plantarum* HEAL 19.

Figure 2:
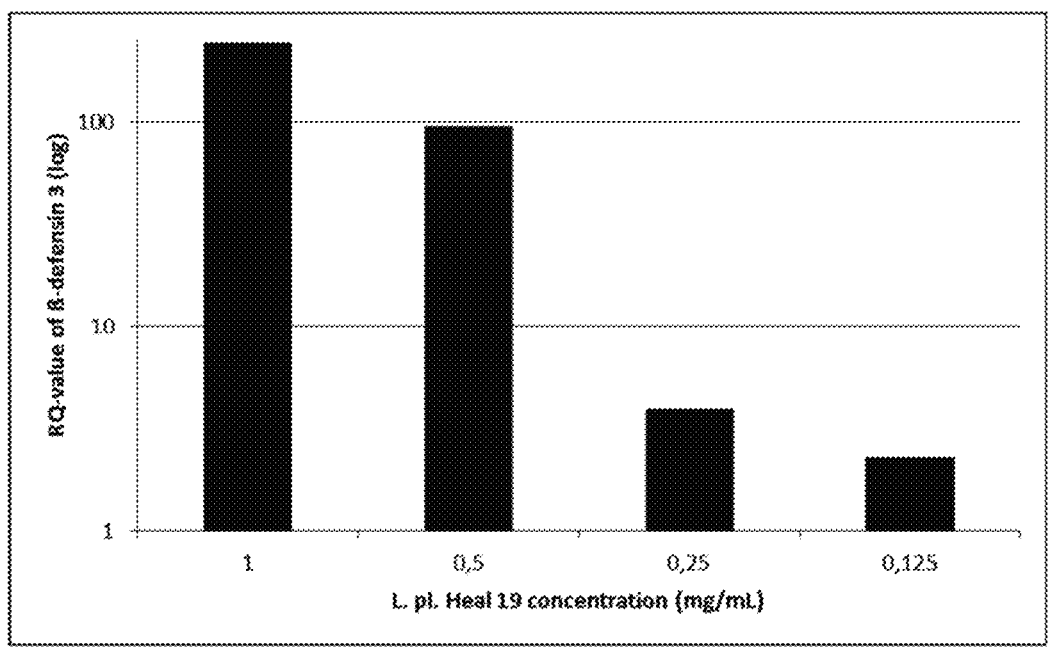

The inductions of AMPs by *L. plantarum* HEAL 19 are concentration dependent. In FIG. 2, concentration dependent induction of β-Defensin 3 are shown. HaCaT keratinocytes were treated for 24 h with various concentrations of *L. plantarum* HEAL 19. This results in calculated RQ-values from 243.6 (by 0.1% *L. plantarum* HEAL 19) to 2.3 (0.0125% *L. plantarum* HEAL 19).

Figure 3:
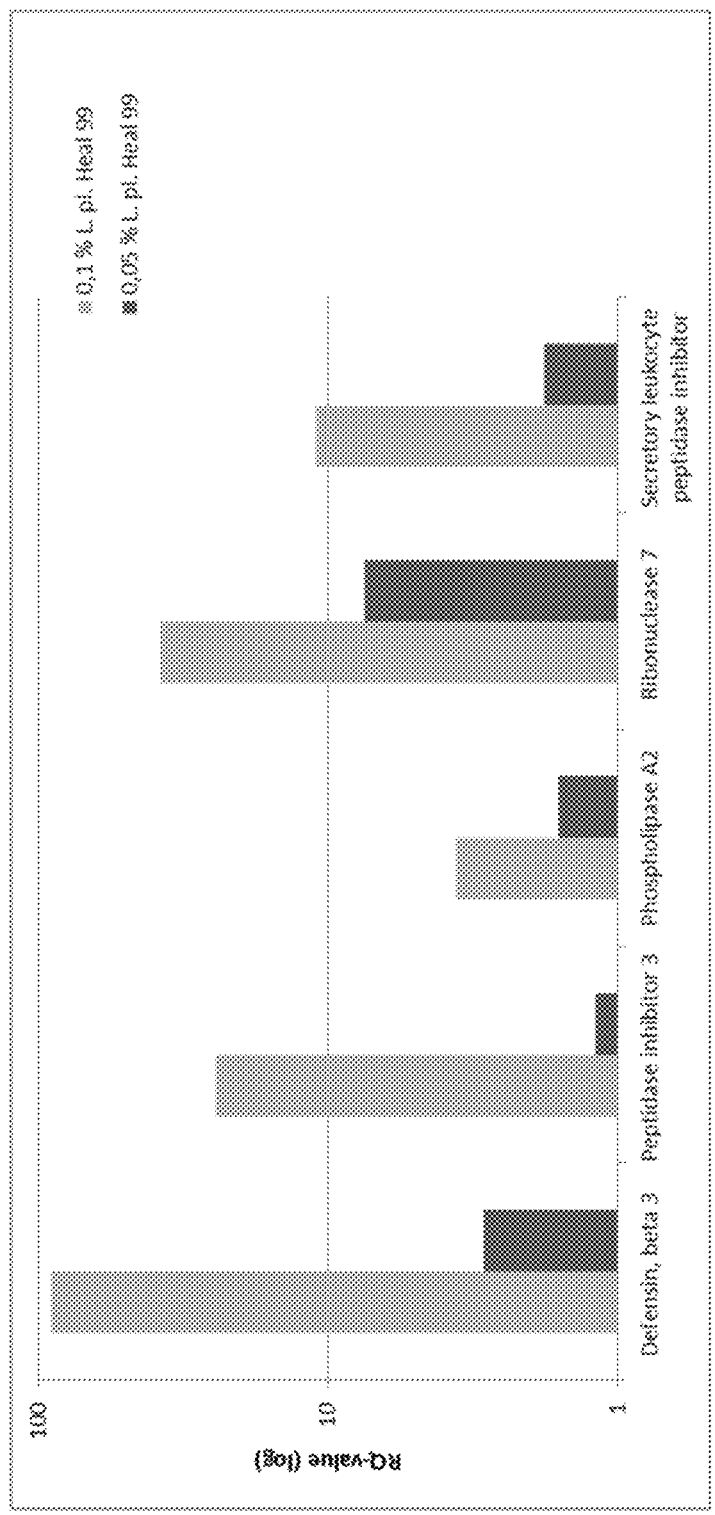

Similar effects can be observed using *L. plantarum* HEAL 99 when HaCaT keratinocytes are treated. FIG. 3 shows exemplarily various inductions of AMP coding genes after 24 h treatment. RNase 7, β-Defensin 3 Peptidase inhibitor 3, Phospholipase A2, and Secretory leukocyte peptidase inhibitor are induced concentration dependently (0.1 and 0.05% were tested) with *L. plantarum* HEAL 99. Similar results have been found using *L. plantarum* Heal 19.

In epidermal 3D human skin models, it has been shown that various AMP coding genes are similarly induced (data not shown).

Example 2: Anti-Inflammatory Effects of *Lactobacillus* Strains (In Vitro/Ex Vivo)

Skin diseases, lesions or irritations mostly correlate with an inflammation of affected skin areas. It was shown that besides the described beneficial effects of the *Lactobacillus* strains, their topical application results in an anti-inflammatory effect. In this connection, the *Lactobacillus* strains support skin health by a further mechanism.

Figure 4:
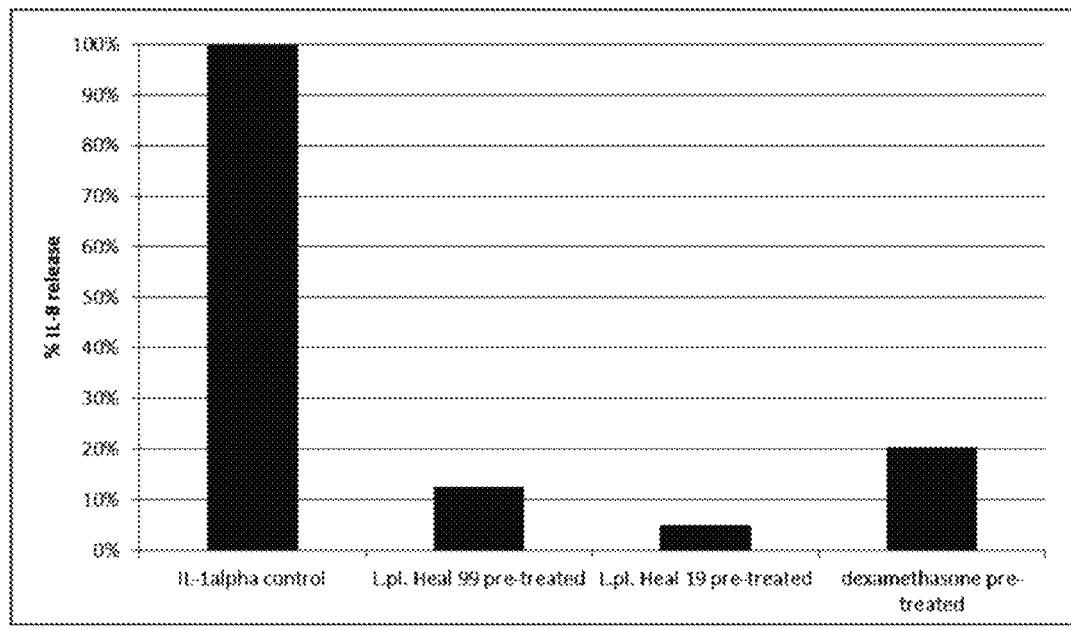

FIG. 4 shows the anti-inflammatory effect of *L. plantarum* HEAL 19 and 99 and dexamethasone, which was included as a positive control. The confluent HaCaT keratinocytes were pre-treated with the test material *L. plantarum* HEAL 99 with 0.1 mg/mL, *L. plantarum* HEAL 19 with 0.25 mg/mL and dexamethasone in 30 µM. After 48 hours incubation keratinocytes were stimulated using 30 ng/mL of pro-inflammatory IL-1alpha for 8 hours. The subsequent release of IL-8 in the cell culture medium was measured using ELISA. By application of the Lactobacilli strains, IL-8 release of HaCaTs could be reduced to 12.6% and 5.1% (Heal 99 and Heal 19), respectively, compared to not pretreated IL-1alpha control. These anti-inflammatory effects are similar to the one of dexamethasone (reduction to 20.4%), indicating the anti-inflammatory potency of these two strains and underlining their potential for use in skin soothing.

Figure 5:
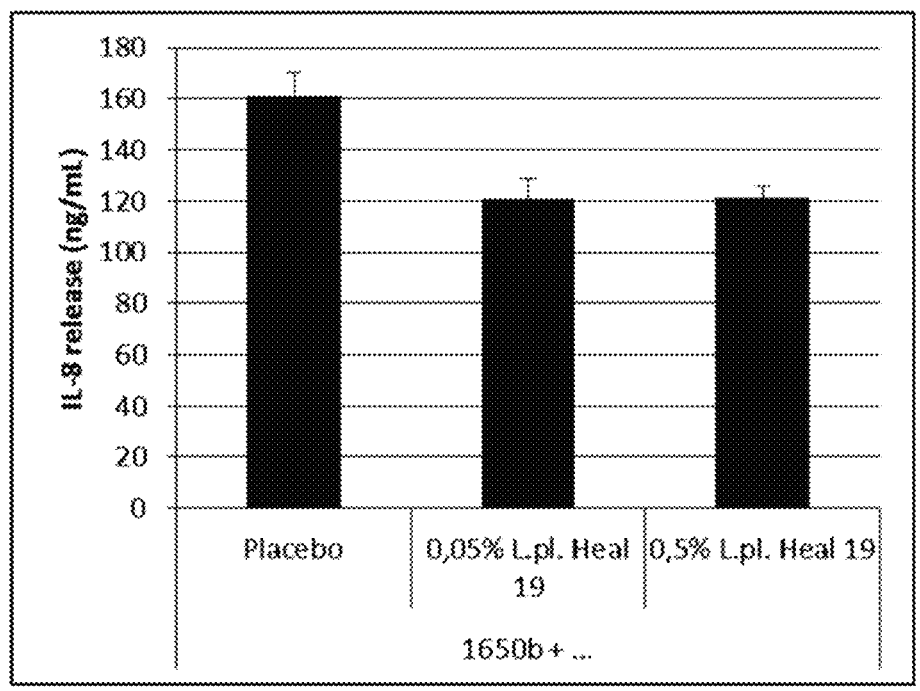
FIG. 5 shows the IL-8 release (axis of ordinates) after treatment of ex vivo human skin model with placebo and *L. plantarum* HEAL 19 formulation and stimulation with diesel particulate 1650b (simulating air pollution)

It has been shown that similar anti-inflammatory effect of *L. plantarum* HEAL 19 can be seen in ex vivo human skin models. As shown in FIG. 5, after stimulation with diesel particulate (1650b), simulating air pollution, the IL-8 detection in cell culture medium is reduced to 75% in *L. plantarum* HEAL 19 treated models, compared to placebo control. Caused by the topical treatment with a cosmetic formulation containing *L. plantarum* HEAL 19 skin's barrier integrity is improved, the skin is calmed and soothed.

Figure 6:
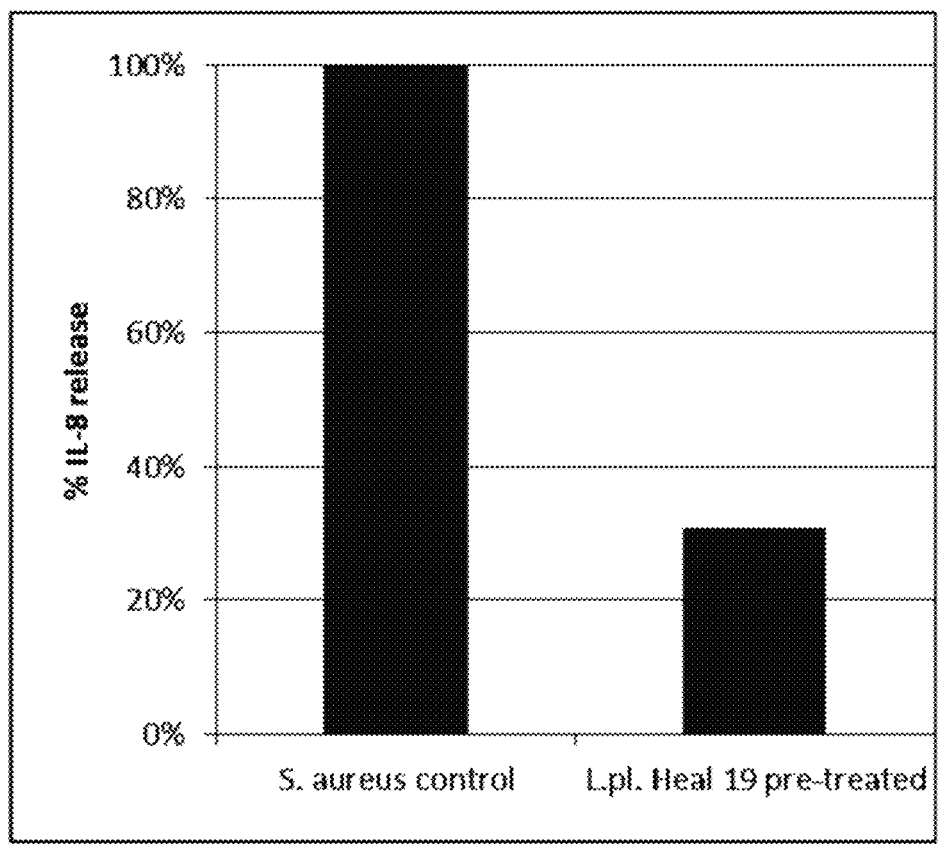
FIG. 6 shows the Interleukin-8 release of HaCaT keratinocytes due to *S. aureus* stimulation after pre-treatment with *L. plantarum* HEAL 19. Comparison is shown to not pre-treated keratinocytes (*S. aureus* control).

Inflammation in skin can not only be induced by pro-inflammatory cytokines but also by bacteria, specifically bacteria pathogenic to the skin, by cell to cell contact. FIG. 6 shows that pretreated HaCaT keratinocytes with 0.25 mg/mL *L. plantarum* HEAL 19 for 48 h reduces drastically *S. aureus* induced inflammation. The IL-8 concentration in the medium can be reduced to 31% compared to only *S. aureus* stimulated control.

*S. aureus* is frequently found in eczemous skin lesions of AD patients and is often responsible for aggravating the disease status and/or encouraging inflammation. The treatment with *L. plantarum* strains on skin results in lower inflammation, it concomitantly reduces redness and the skin is soothed and calmed.

Example 3: Antimicrobial Effect of *Lactobacillus plantarum* HEAL 19 and HEAL 99

It is known that *S. aureus* is consistently found in eczemous skin lesions of AD patients for instance and seems to be important and responsible for aggravating the disease status. Potential infections of the skin can be prevented by inhibiting growth of pathogens, like *S. aureus* by application of the *L. plantarum* strains on skin.

Figure 7:
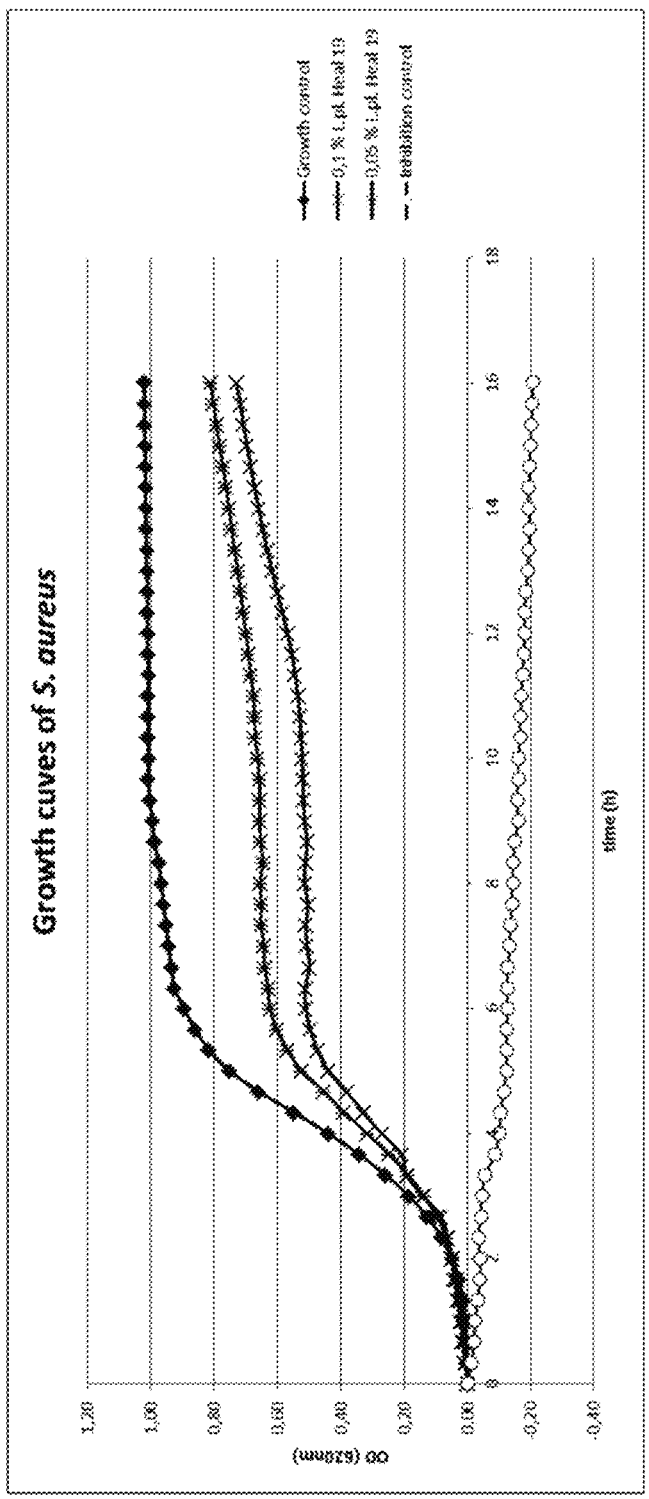
FIG. 7 shows growth inhibition effects of *S. aureus* in a dose dependent way, i.e. when treated with 0.1 and/or 0.05% *L. plantarum* HEAL 19. A comparison is shown to a positive growth control and a negative control (inhibition control, addition of biocide farnesol).

Growth curves of *S. aureus* were created by measuring optical density during 16 h incubation. FIG. 7 shows growth inhibition effects of *S. aureus* when treated with 0.1 and/or 0.05% *L. plantarum* HEAL 19. In summary, topical treatment of skin using the described invention can contribute to reduce and/or prevent inflammation and infection by inhibiting growth of *S. aureus*.

Example 4: Barrier Strengthening

A: Induction of Involucrin and Cytokeratin 14 (CDK14) in Ex Vivo Studies

Figure 8:
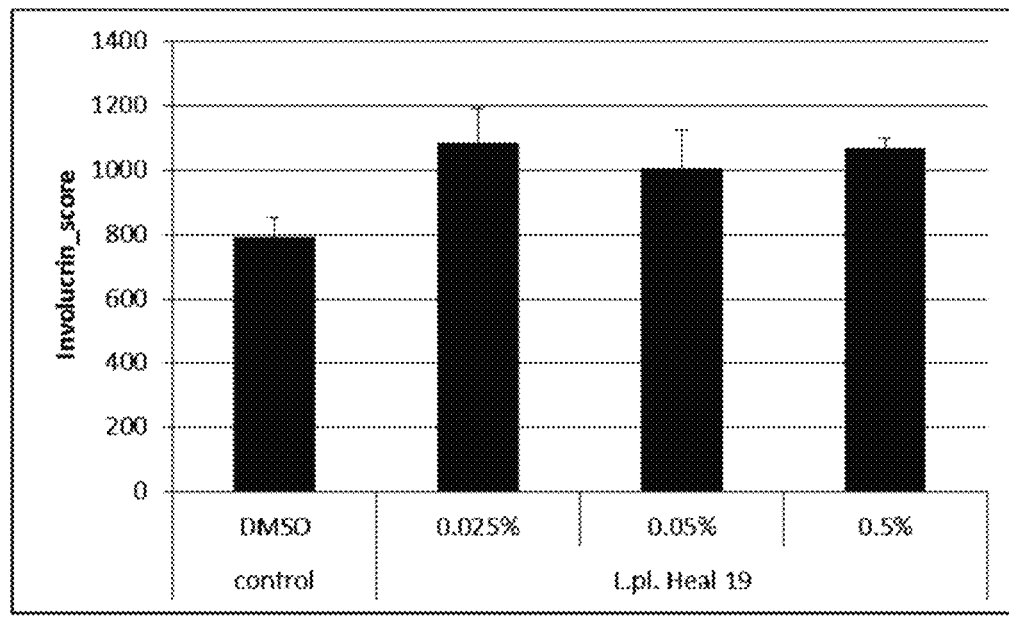
FIG. 8 shows the production of involucrin in ex vivo human skin models (axis of ordinates) after treatment with various concentrations of *L. plantarum* HEAL 19 (x-axis). Comparison is shown to a negative control including only the vehicle (DMSO).
Figure 9:
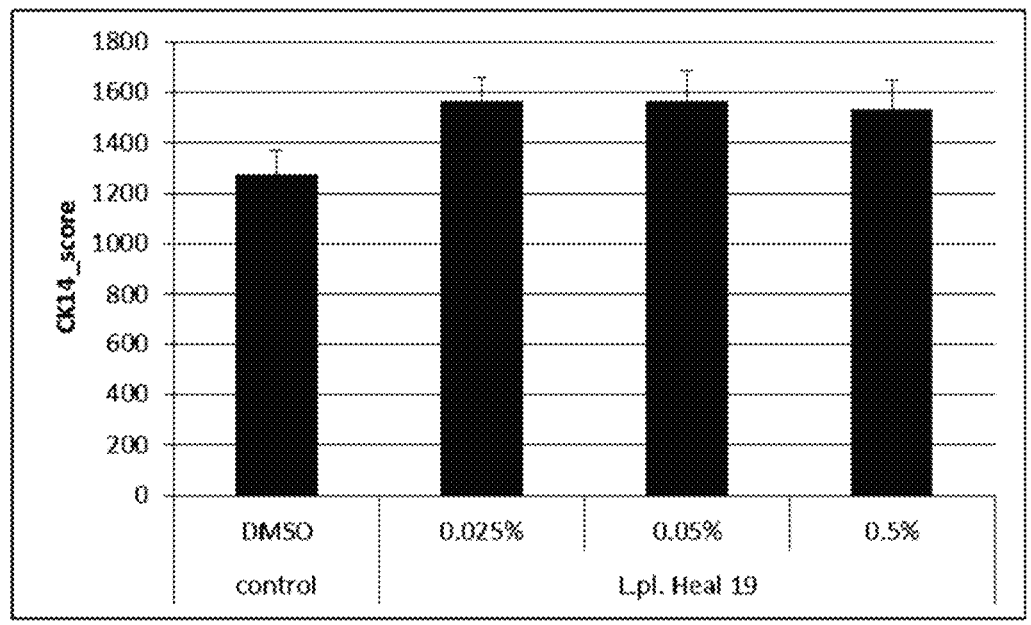
FIG. 9 shows the production of cytokeratin 14 (CK14) contents in ex vivo human skin models (axis of ordinates) after treatment with various concentrations of *L. plantarum* HEAL 19 (x-axis). Comparison is shown to a negative control including only the vehicle (DMSO).

Involucrin is a protein providing structural support to the skin cells and thereby allows the cell to resist invasion by micro-organisms. Cytokeratin 14 is usually found as a heterodimer and forms the cytoskeleton of epithelial cells. Both marker proteins increased by topical treatment using various concentrations of *L. plantarum* HEAL 19 in ex vivo regenerated human skin models, as shown in FIG. 8 and FIG. 9.

It is hereby demonstrated, that topical treatment of skin with the described invention directly leads to a strengthening of skins barrier function.

B: Skin Barrier Integrity

Figure 10:
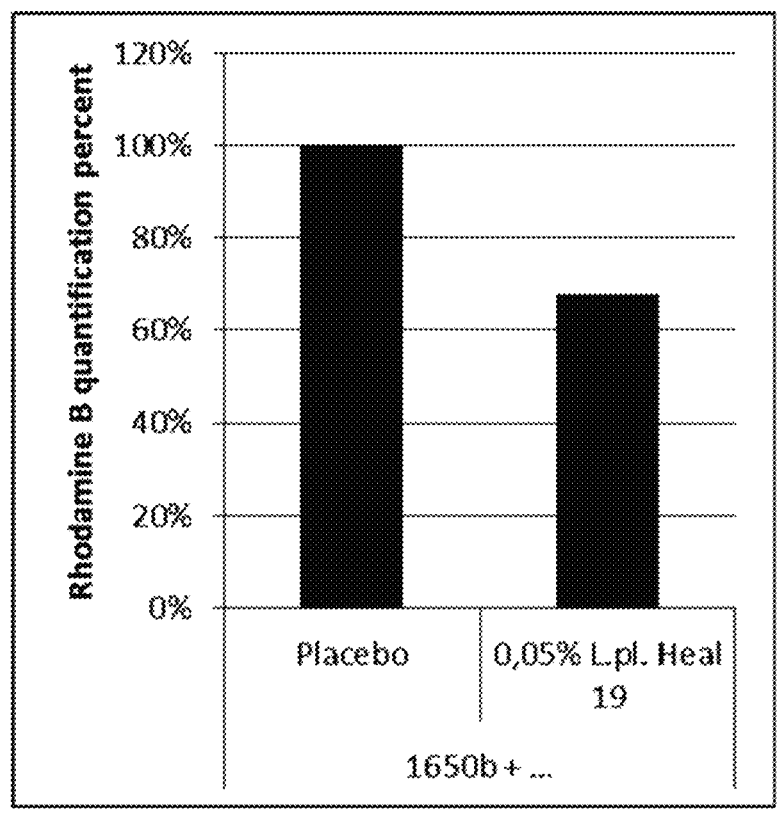
FIG. 10 shows the percentage of Rhodamine B detection (axis of ordinates) after treatment ex vivo with placebo and *L. plantarum* HEAL 19 formulation and stimulation with diesel particulate 1650b.

The invention shows a protective activity on the skin barrier by the reduction of rhodamine B penetration in ex vivo models after treatment with *L. plantarum* HEAL 19 and stimulation with diesel particulate (1650b). The evaluation of skin morphology allows determining whether a compound affects the structure of the treated skin samples. To perform this evaluation, the skin sections have been stained with rhodamine B staining. Following the staining for each skin sample the integrity of the epidermis has been evaluated. FIG. 10 shows that the treatment with *L. plantarum* HEAL 19 improves skin integrity and has a protective activity on the skin barrier function.

C: Barrier Improving Efficacy

The intercellular lipid lamellae in the intercellular space of the stratum corneum, used as a quality measure of the epidermal barrier, were analyzed and quantitatively evaluated. The topical treatment with 0.5% *L. plantarum* HEAL 19 in a skin care formulation leads to an increased repair performance of the 3D epidermal models system for dry skin (FIG. 11). Topical application of a skin care formulation containing the invention strengthens the epidermal barrier function and supports the repair performance of the skin.

Example 5: Hyaluronic Acid Induction in 3D Skin Models

Hyaluronic acid (HYA) plays a series of important roles in skin. It is necessary in skin to maintain epidermal barrier function and the structure of the stratum corneum. Furthermore, it plays an important role in immobilizing water in tissues, in tissue repair or in influencing cell differentiation and proliferation (Weindl et al 2004). All this can be realized with the treatment of the described *L. plantarum* strains.

FIG. 12 shows the increased release of hyaluronic acid in HEPKp 3 dimensional skin models after 8 days treatment with 0.005% *L. plantarum* HEAL 19 or HEAL 99 in cell culture medium. Compared to the medium control the hyaluronic acid release increased to 145 and 115%.

Example 6: Hydration of Skin

A: Filaggrin Release from 3D Skin Models

Increased release of the protein filaggrin into the medium could be detected after 3 to 9 days incubation. FIG. 13 shows increased filaggrin (FLG) release in medium of *Lactobacillus* treated HEPKp 3 dimensional skin models after 8 days. With the used concentrations of 0.05% *L. plantarum* HEAL 19 and HEAL 99, FLG increased in medium to 215 and 150%, respectively.

Topical application of the described invention leads to filaggrin upregulation in human skin and subsequently to a strengthening of the skin barrier and positive effects on skin moisturization.

B: Filaggrin Induction Ex Vivo

The induction of filaggrin due to the topical treatment with the invention was confirmed in studies using ex vivo human skin models. FIG. 14 shows the concentration dependent induction of the filaggrin release after treatment with various concentrations of *L. plantarum* HEAL 19. The higher the applied concentration, the higher the filaggrin release of ex vivo human skin models.

Similar concentration dependent effects were observed in in vitro experiments investigating HEPKp 3D human skin models (data not shown).

Example 7: In Vivo Data

To confirm effects observed in model systems, an in vivo study was performed with a panel of subjects suffering from extra dry skin. Heat-treated *L. plantarum* HEAL 19 was incorporated into a cosmetic cream and applied on inner forearms of panelists. Effects on skin moisture retention capacity (capacitance) and transepidermal water loss (TEWL) were monitored after 0, 7, 14, and 21 days in comparison to untreated and placebo-treated areas.

The in vivo study confirmed effects suggested by molecular biological investigations: capacitance steadily increased over treatment time and effects were significantly stronger than in placebo treatments at all time points. TEWL decreased significantly in the treatments Lactobacilli-containing cream, whereas the placebo had no effect.

These results demonstrate the capacity of the invented heat-treated Lactobacilli strains to increase moisturization and barrier strength of the skin leading to significantly improvement of skin health.

FIGS. 15 and 16 show the water content and the skin barrier strength as determined by capacitance and TEWL over time.

Example 8: Growth Curves for *L. plantarum* Spp

A 96-well MTP was prepared with autoclaved MRS medium (Oxoid CM0359). Three replicate wells were inoculated with each *L. plantarum* spp. strain, using stock cultures maintained in 10% glycerin at −20° C. An inoculum of OD=0.1 was added per well and the 96-well MTP incubated at 37° C. for 16 hours. Growth curves were determined in each well via absorption at 620 nm using a Sunrise Photometer (Tecan, Austria) and Magelan Software. Saline (0.9% Sodium chloride solution) was used as negative growth control.

For calculation, averages of detected absorptions were calculated and plotted in function of time for graphical presentation. The tested strains as well as the obtained growth curves can be seen in FIG. 17.

Formulation Examples 1 to 15

Formulations (compositions) comprising Lactobacilli according to the invention having skin soothing and barrier strengthening effects:
1. Skin lightening day cream o/w
2. Skin-soothing lotion
3. After sun balm, itch reducing
4. Calming body spray
5. Sunscreen lotion (o/w, broadband protection)
6. w/o night cream
7. Scalp soothing Anti dandruff shampoo
8. Self-tanning cream
9. Anti itch barrier repair cream
10. Antiperspirant/deodorant roll-on
11. Emulsion with UV-A/B-broadband protection
12. Sun spray with UV-A/B-broadband protection with low oil content
13. Skin-lightening balm with UV-A/UV-B protection
14. Scalp soothing hair conditioner with UV-B/UV-A protection, rinse off
15: Anti-itch hair conditioner, leave on

| Raw Material Name/INCI | INCI | % BY WEIGHT/FORMULATION EXAMPLE | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| *Lactobacillus plantarum* HEAL19 (pasteurized) | | 0.1 | 0.2 | 0.3 | 0.05 | 0.2 | 0.5 | 0.4 | 0.02 | 0.6 | 0.1 | 0.3 | 0.01 | 1 | 0.1 | 0.15 |
| *Lactobacillus plantarum* HEAL99 (pasteurized) | | 0.05 | 0.1 | 0.1 | 0.02 | 0.1 | 0.1 | 0.1 | 0.05 | 0.2 | 0.1 | 0.05 | 0.02 | 0.2 | 0.3 | 0.15 |
| Abil 350 | Dimethicone | 0.5 | 2.0 | 1.0 | | | | | 0.5 | 0.5 | | 0.3 | | | 0.1 | |
| Allantoin | Allantoin | | 0.2 | 0.1 | | | | | | | 0.25 | | | | | |
| Aloe Vera Gel Concentrate 10/1 * | Water (Aqua). Aloe Barbadensis Leaf Juice | | | 3.0 | | 3.0 | 0.45 | | | | | | | | | |
| Alpinia Leaf Extract Blend | Alpinia Officinarum Leaf Extract. Alpinia conchigera Leaf Extract. Alpinia Blepharocalyx Leaf Extract | | | | | 1.0 | | | | | | | 0.5 | | | |
| Alugel 34 TH | Aluminium Stearate | | | | | | | | | | 1.0 | | | | | |
| Arbutin | β-Arbutin | 0.2 | | | | | | | | | | | | | | |
| (−)-alpha Bisabolol | Bisabolol | | | | | | | | | | | 0.15 | 0.2 | | | 0.1 |

-continued

| Raw Material Name/INCI | INCI | % BY WEIGHT/FORMULATION EXAMPLE | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| Butylene Glycol | Butylene Glycol | | | 5.0 | | | | | | | | 3.0 | | 3.0 | | |
| Carbopol Ultrez-10 | Carbomer | | 0.1 | | | 0.2 | | | | | | 0.2 | | | | |
| Ceramide BIO* | Cetylhydroxy-proline Palmitamide | | 0.1 | | | | | 0.2 | | 0.5 | | | | | | |
| Cetiol OE | Dicaprylyl Ether | | | 4.0 | | | | | | | | | | | | |
| Cetiol SB 45 | Butyrospermum Parkii (Shea Butter) | | | 1.0 | | | | | | | | | | | | |
| Citric Acid 10% sol. | Citric Acid | | 0.4 | | | | | 0.3 | | | | 0.3 | | | | |
| Comperlan 100 | Cocamide MEA | | | | | | | 0.5 | | | | | | | | |
| Crinipan AD | Climbazole | | | | | | | 0.5 | | | | | | | | |
| Curcuma Extract | Curcuma Xanthorrhiza Root Extract | | | | | | | | | | 0.5 | | | | | |
| Curcuma Root Extract | Curcuma Longa (Turmeric) Root Extract | | | 1.5 | | | | | | | | | | | | |
| Dehyquart ACA | Cetrimonium Chloride | | | | | | | | | | | | | | 0.2 | 0.5 |
| Dehyquart SP | Quaternium-52 | | | | | | | | | | | | | | 0.5 | 4.0 |
| Dihydroxyacetone | Dihydroxyacetone | | | | | | | | | 5.0 | | | | | | |
| Dow Corning 246 Fluid | Cyclohexasiloxane and Cyclopentasiloxane | | | | | 2.0 | | | | | | | | | | |
| Dow Corning 345 Fluid | Cyclomethicone | | | | 0.5 | | | | | | | | | | | |
| D-Panthenol | Panthenol | | | 1.0 | | | | | | | | | | | | |
| Dracorin® CE* | Glyceryl Stearate Citrate | 5.0 | | | | | | | 5.0 | 1.5 | | | | | 1.0 | 1.0 |
| Dracorin® GOC* | Glyceryl Oleate Citrate. Caprylic/Capric Triglyceride | | | 2.0 | | | | | | | | | | | | |
| Drago-Beta-Glucan* | Water (Aqua). Butylene Glycol. Glycerin. Avena Sativa (Oat). Kernel Extract | 0.3 | | | | | | | | | | | | | | |
| Dragoderm®* | Glycerin. Triticum Vulgare (Wheat) Gluten. Water (Aqua) | | | | | | | | 2.0 | | | | | | | |
| DragoCalm® | Water (Aqua), Glycerin, Avena Sativa (Oat) Kernel Extract | | 1.0 | 0.8 | | | | | | | | | | | | |
| Drago-Oat-Active* | Water (Aqua). Butylene Glycol. Avena Sativa (Oat) Kernel Extract | | | | 1.0 | | | | | | | | | | | 2.0 |
| Dragosan W/O P* | Sorbitan Isostearate. Hydrogenated Castor Oil. Ceresin. Beeswax (Cera Alba) | | | | | | 6.0 | | | | | | | | | |
| Dragosantol® 100* | Bisabolol | 0.3 | | | 0.1 | 0.3 | 0.2 | | | | 0.1 | 0.1 | | | | |
| Dragoxat® 89* | Ethylhexyl Ethylisononanoate | | | | | | | | | 2.0 | | | | 0.1 | | |
| EDETA BD | Disodium EDTA | | | | | 0.1 | | | 0.1 | | | 0.1 | | | 0.1 | |
| Emulsiphos®* | Potassium Cetyl Phosphate. Hydrogenated Palm Glycerides | | 2.0 | | | 1.5 | | | | 2.0 | | 1.5 | | 0.1 | | |

| Raw Material Name/INCI | INCI | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Ethanol 96% | Ethanol | | | | | | | | 2.0 | | 30.0 | | 13.0 | 5.0 | | |
| Euxyl ® K702 | Dehydroacetic Acid. Benzoic Acid. Phenoxyethanol. Polyaminopropyl Biguanide. Ethylhexylglycerin | | | | | | | | | | 0.5 | | | | | |
| Euxyl ® K712 | Sodium Benzoate. Potassium Sorbate | | | | | | | | | | | 0.2 | | | 0.3 | |
| Extrapone ® Green Tea GW * | Glycerin. Water (Aqua). Camellia Sinensis Leaf Extract | | 0.2 | | | | | | | | | | | | 0.7 | |
| Extrapone ® Rosemary GW* | Glycerin. Water (Aqua). Rosmarinus officinalis (Rosemary) Leaf Extract | | 0.3 | | | | | | | 0.5 | | | | | | |
| Extrapone ® Witch Hazel Distillate colourless* | Propylene Glycol. Hamamelis Virginiana (Witch Hazel) Water. Water (Aqua). Hamamelis Virginiana (Witch Hazel) Extract | | | | | | 1.0 | | | | | | | | | |
| Farnesol* | Farnesol | | | | | | | | | | 0.5 | | | | | |
| Fragrance "Rose"* | Fragrance | | | | | | | | | | | 0.3 | | | | |
| Fragrance "WHITE" * | Fragrance | 0.3 | 0.3 | 0.3 | 0.2 | 0.4 | 0.4 | 0.5 | 0.3 | 0.3 | 1.0 | | 0.5 | 0.4 | 0.5 | 0.1 |
| Frescolat ®MGA* | Menthone Glycerol Acetal | 0.5 | | | | 0.3 | | | | | | | | | | |
| Frescolat ®ML cryst.* | Menthyl Lactate | | | 0.8 | | | | | | | 0.2 | | | | | |
| Frescolat ®X-COOL* | Menthyl Ethylamido Oxalate | | | | | | | | | | | | 1.0 | | | |
| Genapol LRO liquid | Sodium Laureth Sulfate | | | | | | | 37.0 | | | | | | | | |
| Glycerol 85% | Glycerin | 3.0 | 2.0 | 4.0 | | 4.7 | 2.0 | | 1.5 | 3.0 | | | | | | |
| Glyceryl Stearate | Glyceryl Stearate | | 2.0 | | | | | | | 2.0 | | | 2.0 | | 4.0 | |
| Hydrolite ®-5 * | Pentylene Glycol | | | | 5.0 | | | | 3.5 | | | | | | | |
| Hydroviton ® 24* | Water. Glycerin. Sodium Lactate. TEA Lactate. Serine. Lactic Acid. Urea. Sorbitol. Sodium Chloride. Lauryl Diethylenediaminoglycine. Lauryl Aminopropylglycine. Allantoin | | | | | | | | | 1.0 | | | | 4.5 | | |
| Hydroviton ® PLUS* | Water. Pentylene Glycol. Glycerin. Fructose. Urea. Citric Acid. Sodium Hydroxide. Maltose. Sodium PCA. Sodium Chloride. Sodium Lactate. | | 1.0 | | | | | | | | | | 1.0 | | | |

-continued

| Raw Material Name/INCI | INCI | % BY WEIGHT/FORMULATION EXAMPLE | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| | Trehalose. Allantoin. Sodium hyaluronate. Glucose | | | | | | | | | | | | | | | |
| Irgasan DP 300 | Triclosan | | | | | | | | | | 0.3 | | | | | |
| Isoadipate ®* | Diisopropyl Adipate | | | | | | | | | | | | | 1.0 | 1.0 | | |
| Isodragol ®* | Triisononanoin | | 2.0 | | | | | | | 3.0 | | | | | 1.0 | | |
| Isopropyl Palmitate | Isopropyl Palmitate | 4.0 | | | | | | | 4.0 | | | | | | | | |
| Karion F | Sorbitol | | | | | | 2.0 | | | | | | | | | | |
| Keltrol RD | Xanthan Gum | 0.2 | 0.1 | | | 0.2 | | | 0.3 | | | | 0.2 | | | | |
| Kojic acid | Kojic Acid | 1.0 | | | | | | | | | | | 0.5 | 0.2 | 0.3 | | |
| Lanette 16 | Cetyl Alcohol | 1.0 | | | | | | | 1.0 | | | | 1.2 | | | | |
| Lanette E | Sodium Cetearyl Sulfate | | | | | | | | | | | | 0.7 | | | | |
| Lanette O | Cetearyl Alcohol | | 3.0 | | 1.0 | | | | | 2.0 | | | | | | | |
| Lara Care A-200 | Galactoarabinan | | | 0.3 | | | | | | | | | | | | 2.5 | 1.5 |
| Magnesium Chloride | Magnesium Chloride | | | | | | 0.7 | | | | | | | | | | |
| Merquat 550 | Polyquaternium-7 | | | | | | | 0.5 | | | | | | | | | |
| NaOH 10% sol. | Sodium Hydroxide | | | | | | | | | 0.3 | | | | | | | |
| Naringin | 4',5,7-Trihydroxyflavone7-O-Neohesperidoside | | | | | | | | 0.5 | 2.0 | | | | | | | |
| Natrosol 250 HHR | Hydroxyethyl-cellulose | | | | | | | | | | 0.3 | | | | | | |
| Neo Heliopan ® 357* | Butyl Methoxy-dibenzoyl-methane | | | | | 1.0 | | | | | | | | | | | |
| Neo Heliopan ® AP * (10% as sodium salt) | Disodium Phenyl Dibenzimidazole Tetrasulfonate | | | | | 10 | | | | | | | 22.0 | 1.5 | | | |
| Neo Heliopan ® AV* | Ethylhexyl Methoxy-cinnamate | 5.0 | | | | 3.0 | | | | | | | 25.0 | | | | |
| Neo Heliopan ® E1000* | Isoamyl p-Methoxy-cinnamate | | | | | | | | | | | | | | 5.0 | | |
| Neo Heliopan ® HMS* | Homosalate | | | | | | | | | | | | | 5.0 | 5.0 | | |
| Neo Heliopan ® Hydro* (15% as sodium salt) | Phenylbenz-imidazole Sulfonic Acid | | | | | 6.7 | | | | | | | | | | | |
| Neo Heliopan ® MBC * | 4-Methylbenzyl-idene Camphor | | | | | 1.5 | | | | | | | | 33.3 | 10.0 | | |
| Neo Heliopan ® OS* | Ethylhexyl Salicylate | | | | | 5.0 | | | | | | | | | 2.0 | | |
| Neo PCL wssl. N * | Trideceth-9. PEG-5 Ethylhexanoate. Water | | | | | | | | | | | | | | | | |
| Neutral Oil | Caprylic/Capric Triglyceride | 6.0 | | | 4.0 | 2.0 | | | 6.0 | 10.0 | | | 2.0 | | | | 1.0 |
| Oxynex 2004 | BHT | | | | | | 0.1 | | | | | | | | | | |
| Paraffin Oil | Mineral Oil | | | | 4.0 | | | | | | | | | | | | |
| PCL Liquid 100* | Cetearyl Ethylhexoate | 3.0 | 5.0 | | 7.0 | | 12.0 | | 3.0 | | | | 3.0 | | 0.6 | | 0.3 |
| PCL Solid * | Stearyl Heptanoate. Stearyl Caprylate | | 2.0 | | | | | | | | | | | | 3.0 | | |

-continued

| Raw Material Name/INCI | INCI | % BY WEIGHT/FORMULATION EXAMPLE | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| Pemulen TR-2 | Acrylates/C10-30 Alkyl Acrylate Crosspolymer | | | 0.3 | 0.2 | | | | | | | | | | | |
| Polymer JR 400 | Polyquaternium-10 | | | | | | | | | | | | | | | 0.1 |
| Propylene Glycol | Propylene Glycol | | 5.0 | | | | | | | | | | 0.8 | 0.8 | | 0.8 |
| Retinyl Palmitate in Oil | Retinyl Palmitate | | | | | | 0.2 | | | | | | | | | |
| Sepigel 305 | Polyacrylamide. C13-14 Isoparaffin. Laureth-7 | | | | | | | | | 1.0 | | | | | | |
| Sodium Ascorbyl Phosphate | Sodium Ascorbyl Phosphate | 2.0 | | 1.0 | | | | | | | | | | | | |
| Sodium Benzoate | Sodium Benzoate | | | | | | | | 0.5 | | | | | | | |
| Sodium Chloride | Sodium Chloride | | | | | | | | 1.0 | | | | | | | |
| Sodium Hydroxide (10% sol.) | Sodium Hydroxide | | | 0.3 | 0.6 | 0.4 | | | | | | | 2.8 | | | |
| Solubilizer 611674* | PEG-40 Hydrogenated Castor Oil. Trideceth-9. Water (Aqua) | | | | | | | | | | 2.0 | | | 2.2 | | |
| Sun Flower Oil | Helianthus Annuus (Sunflower) Seed Oil | | | | | | 5.0 | | | | | | | | | |
| Sweet Almond Oil | Prunus dulcis | | | | | | 5.0 | | | | | | | | | |
| SymCalmin ® | Pentylene Glycol. Butylene Glycol. Hydroxyphenyl Propamidobenzoic Acid | | | 1.0 | | | | | | 1.0 | | | | | | |
| SymDeo ® B125* | 2-Methyl 5-Cyclohexyl-pentanol | | | | | | | | | | | 0.5 | | | | |
| SymDeo ® MPP* | Dimethyl Phenylbutanol | | | | 0.5 | | | | | | | | | | | |
| Symdiol ®68* | 1.2-Hexanediol. Caprylylglycol. | | | | | | | | | | | | 0.5 | | | |
| Symdiol ®68T * | 1.2-Hexanediol. Caprylylglycol. Tropolone | 0.5 | | | | | | | | | | | | | | |
| SymGlucan ® | Aqua, Glycerin, 1,2-Hexandiol, Caprylyl Glycol, Beta-Glucan | | | | | | | | | | | | | | | 5 |
| SymMatrix ®* | Maltodextrin. Rubus Fruticosus (Blackberry) Leaf Extract | | 0.1 | | | 0.3 | 1.0 | | | | | | | | | |
| SymMollient ® S * | Cetearyl Nonanoate | | | | | | | | | | | | 1.5 | | | |
| SymMollient ® W/S | Trideceth-9, PEG-5 Isononanoate, Water (Aqua) | | | | | | | 0.5 | | | | | | | | 2.0 |
| SymOcide ® PH | Phenoxyethanol, Hydroxy-acetophenone, Caprylyl Glycol, Aqua | | 1.0 | 1.0 | 1.0 | 1.0 | 1.0 | | 1.0 | 1.0 | | | 1.0 | 1.0 | 0.2 | 1.2 |
| SymOcide ®P S * | Phenoxyethanol. Decylene Glycol. 1.2 Hexanediol | | | | | | | 1.0 | | | | | | | | |

-continued

| Raw Material Name/INCI | INCI | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Polyoxyethylene (9) Lauryl Ether | Laureth-9 | | 0.5 | | | | | | | | | | | 1.0 | | |
| SymRelief® 100* | Bisabolol. Zingiber Officinale (Ginger) Root Extract | | | | 0.1 | | | | | | | | | | | |
| SymRelief® S | Bisabolol, Hydroxy-methoxyphenyl Decanone | | | | | | | | | | | 0.2 | | | | |
| SymRepair® 100* | Hexyldecanol. Bisabolol. Cetylhydroxyproline Palmitamide. Stearic Acid. Brassica Campestris (Rapeseed) Sterols | | | | | | | | | 2.0 | | | | | | |
| SymSitive® 1609* | Pentylene Glycol. 4-t-Butylcyclohexanol | | | 1.5 | | | | | | | | 0.5 | | | | |
| SymSol®PF3* | Water. Pentylene Glycol. Sodium Lauryl Sulfoacetate. Sodium Oleoyl Sarcosinate. Sodium Chloride. Disodium Sulfoacetate. Sodium Oleate. Sodium Sulfate | | | | | | | | | | | | | | | 1.5 |
| SymVital® AgeRepair* | Zingiber Officinale (Ginger) Root Extract | 0.1 | | | | 0.1 | | | | | | | | | | |
| SymWhite®377* | Phenylethyl Resorcinol | 0.5 | | | | | | | | | | 0.5 | | 1.0 | | |
| Tego Betain L7 | Cocamidopropyl Betaine | | | | | | 6.0 | | | | | | 1.0 | 1.0 | | |
| Tegosoft PC 31 | Polyglyceryl 3-Caprate | | | | | | | | | 0.3 | | | | | | |
| Tegosoft TN | C12-15 Alkyl Benzoate | | | 5.0 | | 5.0 | | | | | | | | | | |
| Texapon NSO BZ | Sodium Laureth Sulfate | | | | | | | | | | | | | 4.0 | | |
| Tocopherol Acetate | Tocopheryl Acetate | | | 0.5 | | 0.5 | 3.0 | | | 0.3 | | 0.5 | | | | |
| Triethanolamine. 99% | Triethanolamine | | | | | 0.5 | | | | | | | | 0.5 | | |
| Water. demineralized | Water (Aqua) | | | | | | | | ad 100 | | | | | | | |
| Zedoaria Leaf Extract | Curcuma Zedoaria Leaf Extract | 2.0 | | 1.5 | | | | | | | | | | | | |
| Zirkonal L 450 | Aluminium Zirconium Pentachlorohydrate (40% aqueous solution) | | | | | | | | | | 37.0 | | | | | |

CITED REFERENCES

Brogden K A: Antimicrobial formers or metabolic inhibitors in bacteria? Microbiology, 3: 238-250, 2005

Brown K L and Hancock R E W: Cationic host defense (antimicrobial) peptides. Immuology, 18:24-30, 2006

Chung W O, Dale B A: Innate immune response of oral and fore-skin keratinocytes: utilization of different signaling pathway by various bacterial species. Infect Immun, 72:352-8, 2004

Guéniche A, Bastien P, Ovigne J M, Kermici M, Courchay G, Chevalier V, Breton L and Castiel-Higounenc I: Bifidobacterium longum lysate, a new ingredient for reactive skin. Experimental Dermatology, 19: e1-e8, 2010
Harder J, Schröder J M, Glaser R: The skin surface as antimicrobial barrier: present concepts and future outlooks. Experimental Dermatology, 22:1-5, 2013
Ong P Y, Ohtake T, Brandt C, Strickland I, Boguniewicz M, Ganz T, Gallo R L, Leung D Y: Endogenous antimicrobial peptides and skin infections in atopic dermatitis. N Engl J Med. 347:1151-60, 2002
Palmer C N, Irvine A D, Terron-Kwiatkowski A, Zhao Y, Liao H, Lee S P, Goudie D R, Sandilands A, Campbell L E, Smith F J, O'Regan G M, Watson R M, Cecil J E, Bale S J, Compton J G, DiGiovanna J J, Fleckman P, Lewis-Jones S, Arseculeratne G, Sergeant A, Munro C S, El Houate B, McElreavey K, Halkjaer L B, Bisgaard H, Mukhopadhyay S, McLean W H: Common loss-of-function variants of the epidermal barrier protein filaggrin are a major predisposing factor for atopic dermatitis. Nat Genet, 38:441-6, 2006
Peral M C, Huaman Martinez M A, Valdez J C: Bacteriotherapy with *Lactobacillus plantarum* in burns. Int Wound J, 6:73-81, 2009
Sakaguchi S, Miyara M, Costantino C M Hafler D A: FOXP3+ regulatory T cells in the human immune system. Nature Reviews Immunology, 10:490-500, 2010
Weindl G, Schaller M, Schafer-Korting M, Korting H C: Hyaluronic acid in the treatment and prevention of skin diseases: molecular biological, pharmaceutical and clinical aspects. Skin Pharmacol Physiol. 17(5):207-13, 2004
Wiesner J, Vilcinskas A: Antimicrobial peptides. The ancient arm of the human immune system. Virulence, 1:5, 440-464, 2010
Yong C C, Khoo B Y, Sasidharan S, Piyawattanametha W, Kim S H, Khemthongcharoen N, Chuah L O, Ang M Y, Liong M T: Activity of crude and fractionated extracts by lactic acid bacteria (LAB) isolated from local dairy, meat, and fermented products against *Staphylococcus aureus*. Ann Microbiol, 65:1037-1047, 2015
Zasloff M: Antimicrobial peptides of multicellular organism. Nature, 415:389-395, 2012

What is claimed is:

1. A method for improving the appearance of non-mucosal skin comprising topically applying to the non-mucosal skin a topical composition comprising:
 (a) attenuated or dead *Lactobacillus plantarum* HEAL 19 (DSM 15313) having an intact physical structure, wherein the *Lactobacillus plantarum* HEAL 19 (DSM 15313) have been heat-treated at a temperature of 60 to 121° C. for 1 second to 120 minutes;
 (b) one or more carriers, excipients, further active ingredients, or a combination thereof;
 (c) one or more preservatives; and
 (d) water;
 wherein the method improves the appearance of the non-mucosal skin by reducing or preventing skin irritation, dry skin, rash, acne, or skin aging.

2. The method of claim 1, wherein the method treats or improves a skin condition.

3. The method of claim 2, wherein the skin condition is loss of skin barrier function, an inflammatory skin condition, growth of a pathogenic microorganism, or a combination thereof.

4. The method of claim 2, wherein the skin condition is atopic dermatitis, a microbial infection, dry skin, itchy skin, sensitive skin, inflammation of the skin, rosacea, psoriasis, rash, acne, or a combination thereof.

5. The method of claim 1, wherein the *Lactobacillus plantarum* HEAL 19 (DSM 15313), is applied to the skin in a pharmaceutical or cosmetic composition, the pharmaceutical or cosmetic composition comprising:
 (a) 0.01 to 5% dry weight, based on a total weight of the pharmaceutical or cosmetic composition, of the *Lactobacillus plantarum* HEAL 19 (DSM 15313) in an amount sufficient for improving the appearance of the skin by reducing or preventing skin irritation, dry skin, rash, acne, or skin aging; and
 (b) one or more carriers, excipients, further active ingredients, or a combination thereof,
 wherein the pharmaceutical or cosmetic composition comprises at least $10^8$ cells of the *Lactobacillus plantarum* HEAL 19 (DSM 15313) per gram of the pharmaceutical or cosmetic composition.

6. The method of claim 5, wherein the *Lactobacillus plantarum* HEAL 19 (DSM 15313) have been subjected to freeze-drying, spray-drying, or granulating.

7. The method of claim 6, wherein the *Lactobacillus plantarum* HEAL 19 (DSM 15313) have been freeze-dried, spray-dried, or granulated with a carrier selected from inulin, starch, gummi *arabicum*, whey protein, skim milk powder, maltodextrin, or a combination thereof.

8. The method of claim 5, wherein the pharmaceutical or cosmetic composition is in the form of an oil-in-water or water-in-oil emulsion, an ointment, a crème, a lotion, or a gel.

9. The method of claim 8, wherein the method treats dry skin and comprises applying the pharmaceutical or cosmetic composition to dry skin.

10. The method of claim 8, wherein the method treats atopic dermatitis and comprises applying the pharmaceutical or cosmetic composition to skin suffering from atopic dermatitis.

11. The method of claim 8, wherein the method treats a microbial infection and comprises applying the pharmaceutical or cosmetic composition to skin suffering from a microbial infection.

12. The method of claim 8, wherein the method treats itchy or sensitive skin and comprises applying the pharmaceutical or cosmetic composition to the itchy or sensitive skin.

13. The method of claim 8, wherein the method treats inflammation of the skin and comprises applying the pharmaceutical or cosmetic composition to inflamed skin.

14. The method of claim 8, wherein the method treats rosacea, psoriasis, rash, a combination thereof and comprises applying the pharmaceutical or cosmetic composition to skin suffering from rosacea, psoriasis, rash, or a combination thereof.

15. A method for treating non-mucosal skin comprising topically applying a pharmaceutical or cosmetic composition to non-mucosal skin suffering a skin condition selected from atopic dermatitis, a microbial infection, dryness, itchiness, inflammation, rosacea, psoriasis, rash, acne, or a combination thereof, the pharmaceutical or cosmetic composition comprising:
 (a) 0.01 to 5% dry weight, based on a total weight of the pharmaceutical or cosmetic composition, of non-viable *Lactobacillus plantarum* HEAL 19 (DSM 15313) having an intact physical structure; and
 one or more further carriers, excipients, further active ingredients, or a (b) combination thereof;
 wherein the pharmaceutical or cosmetic composition comprises at least $10^8$ cells of the non-viable *Lactobacillus plantarum* HEAL 19 (DSM 15313) per gram of the pharmaceutical or cosmetic composition, and is in the form of an oil-in-water or water-in-oil emulsion, an ointment, a crème, a lotion, or a gel.

16. The method of claim 1, wherein the topical composition further comprises *Lactobacillus plantarum* HEAL 99 (DSM 15316).

17. The method of claim 16, wherein the *Lactobacillus plantarum* HEAL 19 (DSM 15313) and *Lactobacillus plantarum* HEAL 99 (DSM 15316) have been subjected to freeze-drying, spray-drying, or granulating with a carrier selected from inulin, starch, gummi *arabicum*, whey protein, skim milk powder, maltodextrin, or a combination thereof, and wherein the *Lactobacillus plantarum* HEAL 19 (DSM 15313) and *Lactobacillus plantarum* HEAL 99 (DSM 15316), and the carrier, are in a weight ratio of 1:9 to 3.7.

* * * * *